(12) United States Patent
Eastep et al.

(10) Patent No.: US 12,268,794 B2
(45) Date of Patent: Apr. 8, 2025

(54) SYSTEMS AND METHODS FOR DECONTAMINATION OF PATIENT CARE EQUIPMENT AND INTERIOR SPACES

(71) Applicant: Battelle Memorial Institute, Columbus, OH (US)

(72) Inventors: Jon Eastep, Baltimore, OH (US); William Richter, Hilliard, OH (US); Kevin Yugulis, Columbus, OH (US); Ryan Kaufman, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 315 days.

(21) Appl. No.: 17/211,572

(22) Filed: Mar. 24, 2021

(65) Prior Publication Data
US 2021/0346552 A1    Nov. 11, 2021

Related U.S. Application Data

(60) Provisional application No. 63/124,000, filed on Dec. 10, 2020, provisional application No. 63/022,361, (Continued)

(51) Int. Cl.
| A61L 2/20 | (2006.01) |
| A61L 2/28 | (2006.01) |
| A61L 9/03 | (2006.01) |

(52) U.S. Cl.
CPC ............... *A61L 2/208* (2013.01); *A61L 2/28* (2013.01); *A61L 9/032* (2013.01);
(Continued)

(58) Field of Classification Search
CPC ..... A61L 2/10; A61L 2/24; A61L 2/26; A61L 2/0047; A61L 2/0052; A61L 9/30;
(Continued)

(56) References Cited

U.S. PATENT DOCUMENTS

| 5,527,507 A | * | 6/1996 | Childers | ................. A61L 2/208 422/298 |
| 5,607,652 A | | 3/1997 | Hellmuth et al. | |

(Continued)

OTHER PUBLICATIONS

International Search Report from corresponding PCT Appln. No. PCT/US21/23964, dated Mar. 24, 2021.
(Continued)

*Primary Examiner* — Jennifer Wecker
*Assistant Examiner* — Brady C Pilsbury
(74) *Attorney, Agent, or Firm* — Grossman, Tucker, Perreault & Pfleger, PLLC; Donald J. Perreault

(57) ABSTRACT

A system for decontamination of patient care equipment and a system for decontamination of an interior space. In some embodiments, a decontaminant distributor is provided in an enclosure and coupled to a decontaminant generator system. The decontaminant generator system may include a decontaminant generator removably coupled to the decontaminant distributor at an exterior of the enclosure for allowing the decontaminant generator to be removed and connected to another decontaminant distributor associated with another system for decontamination of patient care equipment. An air agitation system may be provided in the enclosure for agitating air and decontaminant in the enclosure. In some embodiments, a portable system may be transported to an interior space for decontaminating the items in the space using hot-air decontamination. A rack configuration for drying patient care equipment may include at least one duct having openings in a top and/or bottom surface thereof for directing pressurized dry air toward the patient care equipment.

21 Claims, 15 Drawing Sheets

Related U.S. Application Data filed on May 8, 2020, provisional application No. 63/016,928, filed on Apr. 28, 2020, provisional application No. 63/012,861, filed on Apr. 20, 2020, provisional application No. 63/001,313, filed on Mar. 28, 2020.

(52) U.S. Cl.
CPC ..... *A61L 2202/122* (2013.01); *A61L 2202/14* (2013.01); *A61L 2202/16* (2013.01); *A61L 2202/24* (2013.01); *A61L 2209/111* (2013.01); *A61L 2209/14* (2013.01); *A61L 2209/211* (2013.01)

(58) Field of Classification Search
CPC ........... A61L 2202/11; A61L 2202/122; A61L 2202/14; A61L 2202/15; A61L 2202/16; A61L 2202/21; A61L 2202/24; A61L 2202/25; A61K 39/12; A61K 2039/5252; A61M 16/00; A61M 16/0666; B01D 53/007; B01D 2259/804; C02F 1/325; C02F 2201/3227; C02F 2201/326; F24F 8/22; F24F 13/20; F24F 2013/205; H05K 1/038; H05K 2201/05; G06F 3/0482; G06F 3/0487; Y02A 50/20
See application file for complete search history.

(56) References Cited

U.S. PATENT DOCUMENTS

| | | | |
|---|---|---|---|
| 5,882,590 A | 3/1999 | Stewart et al. | |
| 6,852,279 B2* | 2/2005 | Williams | H04J 14/0227 422/4 |
| 7,908,791 B1* | 3/2011 | Brash | A01M 13/003 43/125 |
| 8,153,078 B2 | 4/2012 | Bacik et al. | |
| 8,865,065 B2 | 10/2014 | Kain et al. | |
| 9,327,040 B2 | 5/2016 | Kain et al. | |
| 9,871,399 B2 | 1/2018 | Mittleman et al. | |
| 2003/0138344 A1* | 7/2003 | Mielnik | A61L 2/206 422/4 |
| 2003/0138347 A1* | 7/2003 | Lin | A61L 2/26 422/1 |
| 2007/0253859 A1* | 11/2007 | Hill | A61L 9/22 422/305 |
| 2008/0279720 A1 | 11/2008 | Meilander et al. | |
| 2010/0226821 A1* | 9/2010 | Ricciardi | A61L 2/24 422/295 |
| 2013/0216438 A1* | 8/2013 | Hill | A61L 2/208 422/187 |
| 2018/0038041 A1* | 2/2018 | Longinotti-Buitoni | D06F 35/001 |
| 2019/0030198 A1* | 1/2019 | Mauzerall | A61L 2/07 |
| 2019/0314535 A1* | 10/2019 | Golkowski | A61L 2/208 |
| 2022/0125965 A1* | 4/2022 | Alva | A61L 2/202 |

OTHER PUBLICATIONS

Written Opinion from corresponding PCT Appln. No. PCT/US21/23964, dated Jul. 28, 2021.

* cited by examiner ary applicability of decontamination rooms in hospitals and equipment and interior spaces.

SYSTEMS AND METHODS FOR DECONTAMINATION OF PATIENT CARE EQUIPMENT AND INTERIOR SPACES

CROSS-REFERENCE TO RELATED APPLICATIONS

The present application claims the benefit of the filing date of U.S. Provisional application Ser. No. 63/001,313, filed Mar. 28, 2020, U.S. Provisional Application Ser. No. 63/012,861, filed Apr. 20, 2020, U.S. Provisional Application Ser. No. 63/016,928, filed Apr. 28, 2020, U.S. Provisional Application Ser. No. 63/022,361, filed May 8, 2020 and U.S. Provisional Application Ser. No. 63/124,000, filed Dec. 10, 2020, the entire teachings of which applications are hereby incorporated herein by reference.

TECHNICAL FIELD

The present application relates to generally to decontamination and, more particularly, to systems and methods for decontamination of patient care equipment and interior spaces.

BACKGROUND

Decontamination of equipment used in providing health care can be challenging and is a significant factor in preventing transmission of infectious diseases. Various items used by heath care professionals may come into contact with, or in close proximity to, infected patients and/or may be extensively handled or used by health care professionals after exposure to infected patients. Such items include just about any item that may be found in a health care setting, such as masks, face shields, gowns and footwear; surgical equipment, computer equipment, beds, wheelchairs, IV poles, blood pressure monitors, cables, hoses, carts, etc. These items may be considered "patient care equipment", which, as used herein, shall refer to any item that may have been exposed to an infectious disease in a health care setting. Use of patient care equipment by several people can increase the risk of transmission of infectious disease.

Various methods to disinfect patient care items have been developed and are widely used. In some methods, a room in a hospital is established as a decontamination room. Patient care items are placed in the room and are exposed to a decontaminant, e.g., a sterilizing light, radiation, or spray. In the event there is a need to rapidly respond to an outbreak of disease, these decontamination rooms might be overwhelmed and incapable of supporting the volume of decontamination required by health care professionals. Unfortunately, these decontamination rooms require significant labor and cost to construct and build and are difficult to rapidly deploy in an emergency situation outside of a hospital, such as in a field hospital or emergency treatment setting.

Interior spaces, which can contain porous materials, including paper, wood, and soft surfaces (e.g., carpet, cubicle walls), also may require decontamination. Common decontamination solutions are excellent non-porous surface decontaminants; however, they may be unable to effectively decontaminate, without saturating or destroying, many porous materials. Removing materials, like paper or other porous materials, from a contaminated area can expose individuals to infectious agents.

BRIEF DESCRIPTION OF THE DRAWINGS

Features of this disclosure, and the manner of attaining them, will become more apparent and better understood by reference to the following description of embodiments described herein taken in conjunction with the accompanying drawings, wherein.

DETAILED DESCRIPTION

Figure 1:
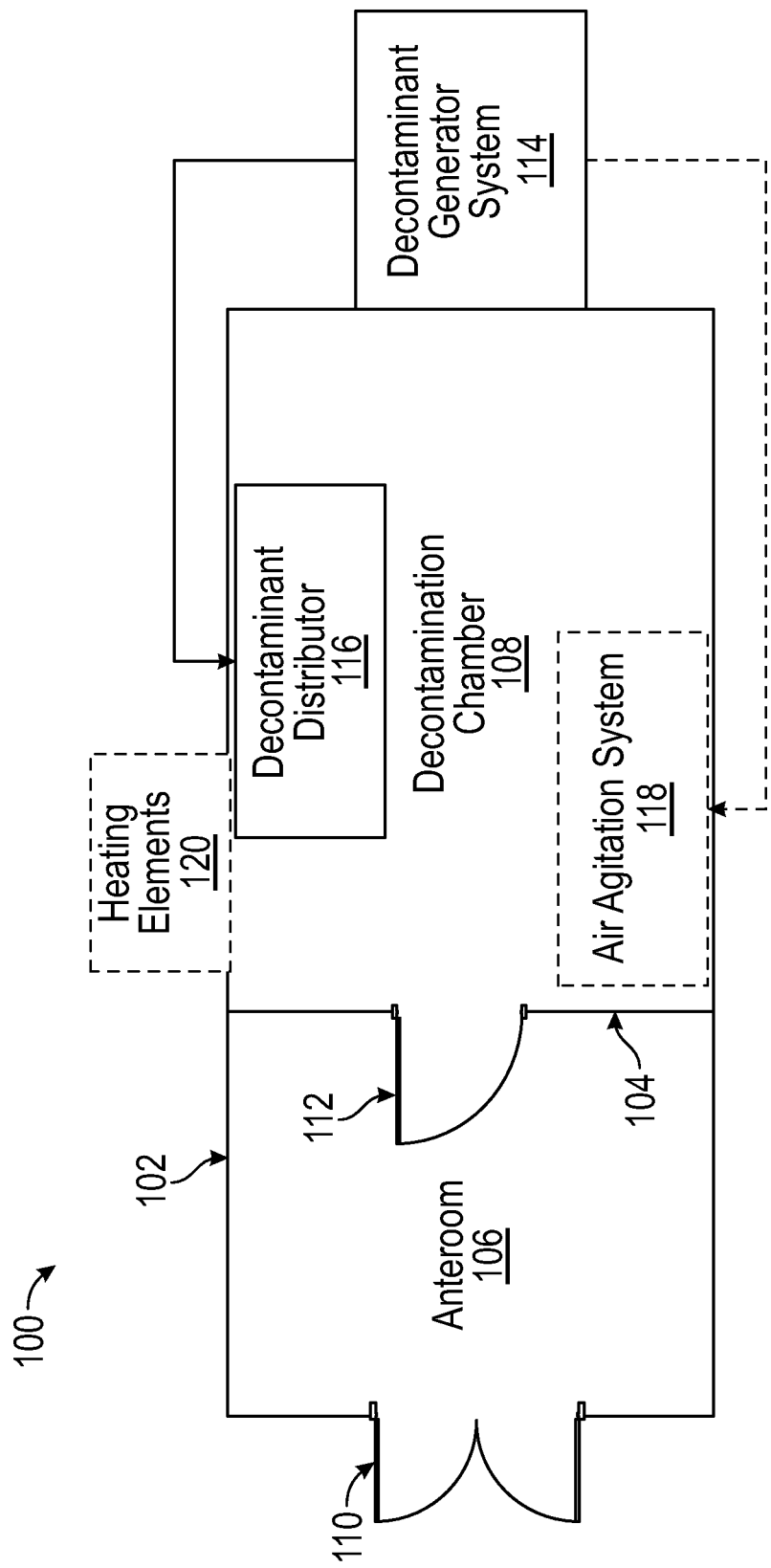
FIG. 1 is a simplified block diagram of one example of a system consistent with the present disclosure.

The present disclosure is not limited in its application to the details of construction and the arrangement of components set forth in the following description or illustrated in the drawings. The examples described herein may be capable of other embodiments and of being practiced or being carried out in various ways. Also, it may be appreciated that the phraseology and terminology used herein is for the purpose of description and should not be regarded as limiting as such may be understood by one of skill in the art. Throughout the present description, like reference characters may indicate like structure throughout the several views, and such structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable, and not exclusive.

In some embodiments, a system for decontamination of patient care equipment consistent with the present disclosure generally includes an enclosure that may be rapidly deployed and relocated. In some embodiments, multiple enclosures may be provided to rapidly expand the capacity for decontaminating patient care items. The enclosure may include an anteroom and a decontamination chamber. The anteroom may provide a space for a person to disrobe contaminated items, such as personal protective equipment, and may be sealed to prevent escape of infectious agents. The decontamination chamber may be accessible from the anteroom through a door. Patient care items may be placed in the decontamination chamber. A decontamination generator on the outside of the enclosure may source a decontaminant, e.g., radiation, spray, etc. in the decontamination chamber to decontaminate the patient care items therein. One or more components of the decontamination generator may be portable to allow use with other enclosures to provide decontamination capability in multiple enclosures using the same one or more components of the decontamination generator. In embodiments wherein the decontamination generator provides a decontaminating spray or vapor, such as a hydrogen peroxide vapor (HPV), in the decontamination chamber, the decontamination chamber may include an air agitation system to agitate the air and the decontaminating vapor to distribute the decontaminating vapor over the patient care items.

Systems and methods consistent with the present disclosure may be implemented in a variety of configurations. FIG. 1, for example, is a simplified block diagram of one example embodiment of a system 100 consistent with the present disclosure. The illustrated system 100 includes an enclosure 102 with a partition 104 therein to define an anteroom 106 and a decontamination chamber 108. The anteroom may act as a sealed airlock. One or more entry doors 110 allow access to the anteroom 106 and one or more decontamination chamber doors 112 allow entry from the anteroom 106 into the decontamination chamber 108. A decontaminant generator system 114 is provided at the outside of the enclosure 102 for causing a decontaminant to emanate from one or more decontaminant distributors 116 in the decontamination chamber 108. An optional air agitation system 118 may be provided in the decontamination chamber 108 for agitating the air and the decontaminant within the decontamination chamber 108. One or more heating elements 120 may be coupled to the exterior surface of the enclosure 102 for heating the interior of the decontamination chamber 108 to a desired temperature.

The enclosure 102 may take a variety of configurations but generally provides an enclosed space for at least one decontamination chamber 108. The enclosure 102 is free standing and portable and can be loaded on a truck for transport to a desired location. In some embodiments, the enclosure 102 may not define a separate anteroom 106 and may, instead, define only one or more decontamination chambers 108. In some embodiments multiple anterooms 106 may be provided, e.g., an anteroom 106 at the front and rear of the enclosure 102 may be provided with one or more decontamination chambers 108 therebetween. The enclosure 102 may be constructed from any material suitable for establishing an enclosed space and containing the decontaminant provided by the decontaminant generator system.

In some embodiments, the enclosure 102 may be defined by rigid side, front, rear, top and bottom walls and in other embodiments one or more of the walls may be constructed from a flexible material, such as plastic sheeting. In some embodiments, the enclosure 102 may be constructed using a known and commercially available shipping container.

The decontaminant generator system 114 may be any system configured to cause decontaminant to emanate from the decontaminant distributor 116 and to generate a negative pressure in the enclosure. The decontaminant may be selected to decontaminate biological contaminates, such as SARS-Cov-2 or COVID-19, from patient care equipment. A variety of decontaminant generator system 114 and decontaminant distributors 116 are known. For example, in some embodiments, the decontaminant distributor 116 may include one or more electromagnetic radiation sources, e.g., an ultraviolet (UV) or microwave radiation source, and the decontaminant generator system 114 may be configured to energize the decontaminant distributor 116 to emanate UV or microwave radiation. In some embodiments, the decontaminant generator system 114 and distributor may be configured of generate HPV and the decontaminant distributor 116 may include piping and one or more manifolds for distributing the HPV in the decontamination chamber 108.

One example of a decontaminant generator system 114 for producing HPV (also referred to herein as VPHP for Vapor Phase Hydrogen Peroxide) is the Bioquell L-4 mobile hydrogen peroxide vapor generator commercially available from Bioquell, Inc. of Horsham, Pa., USA. In other embodiments, the decontaminant generator system 114 may be configured for producing hot air to provide hot air decontamination (HAD) of equipment in the decontamination chamber. For example, the decontaminant generator system may be configured as a MIDS system, as described herein, used inside the decontamination chamber to decontaminate patient care equipment and/or porous materials.

The optional air agitation system 118 may include one or more fans or blowers disposed within the decontamination chamber 108 for agitating the air and decontaminant to distribute the decontaminant within decontamination chamber 108 so that it is imparted on the patient care equipment. For example, in an embodiment wherein the decontaminant is HPV, the HPV may emanate from one or more manifolds of the decontaminant distributor 116 and the air agitation system 118 may distribute the HPV over the patient care equipment.

In some embodiments, calibrated chemical indicators may be placed throughout the decontamination chamber to confirm homogenous distribution of the decontaminant in the decontamination chamber to achieve a desired decontamination effect. The outputs of the indicators may be used as feedback to control the agitation system 118 for uniformly distributing the decontaminant in the decontamination chamber. This provides a high level of exposure of the patient care equipment to the decontaminant.

In general, in a method of decontaminating patient care equipment consistent with the present disclosure, a healthcare worker may enter the anteroom 106 with the patient care equipment through the entry doors 110. A negative pressure may be generated in the enclosure using a blower and ductwork portion of the decontaminant generator system so that contaminants do not escape the enclosure. The worker may disrobe personal protective gear, such as a mask, face shield, gown, gloves, footwear, etc. for decontamination and/or pass the personal protective gear and other patient care equipment into the decontamination chamber 108 through the decontamination room door 112. Once the patient care equipment is in the decontamination chamber 108, workers may exit the decontamination chamber and enter the anteroom. Once in the anteroom the workers may close and seal the decontamination room door 112, spray themselves with a decontaminant such as ethanol and then close and seal the entry doors. The decontaminant generator system 114 may then be energized to cause the decontaminant distributor 116 to emanate decontaminant thereby imparting the decontaminant onto the patient care equipment. The air agitation system 118 may be energized to uniformly distribute vaporized or aerosolized decontaminant in the decontamination chamber 108.

In some embodiments, at least a portion of the decontaminant generator system 114 may be removable and portable for use with another enclosure 102. In these embodiments, the removable portion of the decontaminant generator system 114 may cause decontaminant to be emanate from the decontaminant distributor 116 of a first enclosure and then may be transported to one or more other enclosures 102 to cause decontaminant to emanate from the decontaminant distributors 116 of the other enclosures 102. For example, in an embodiment wherein the decontaminant is HPV, the removable portion of the decontaminant generator system 114 may be the portion that generates the HPV. Once the HPV has been introduced to the decontamination chamber 108 of a first enclosure 102 the removable portion may be removed and transported to a second enclosure 102 to distribute the HPV in the decontamination chamber 108 of the second enclosure 102. While the HPV is being distributed in the second enclosure 102, the HPV in the first enclosure 102 decontaminates the patient care equipment and, and in some embodiments, may be at least partially actively or passively degassed from the first enclosure.

In some embodiments, for example, a two or 2.5-hour decontamination phase may be followed by a four-hour degassing phase where the HPV is withdrawn from the decontamination chamber 108 by a blower portion of the decontaminant generator system 114. During the degassing phase, the removable portion of the decontaminant generator system 114 may be transported to a second enclosure 102 for use in decontaminating patient care equipment in the decontamination chamber 108 of the second enclosure 102. This provides an efficient and cost-effective approach for decontaminating large quantities of patient care equipment.

Figure 2:
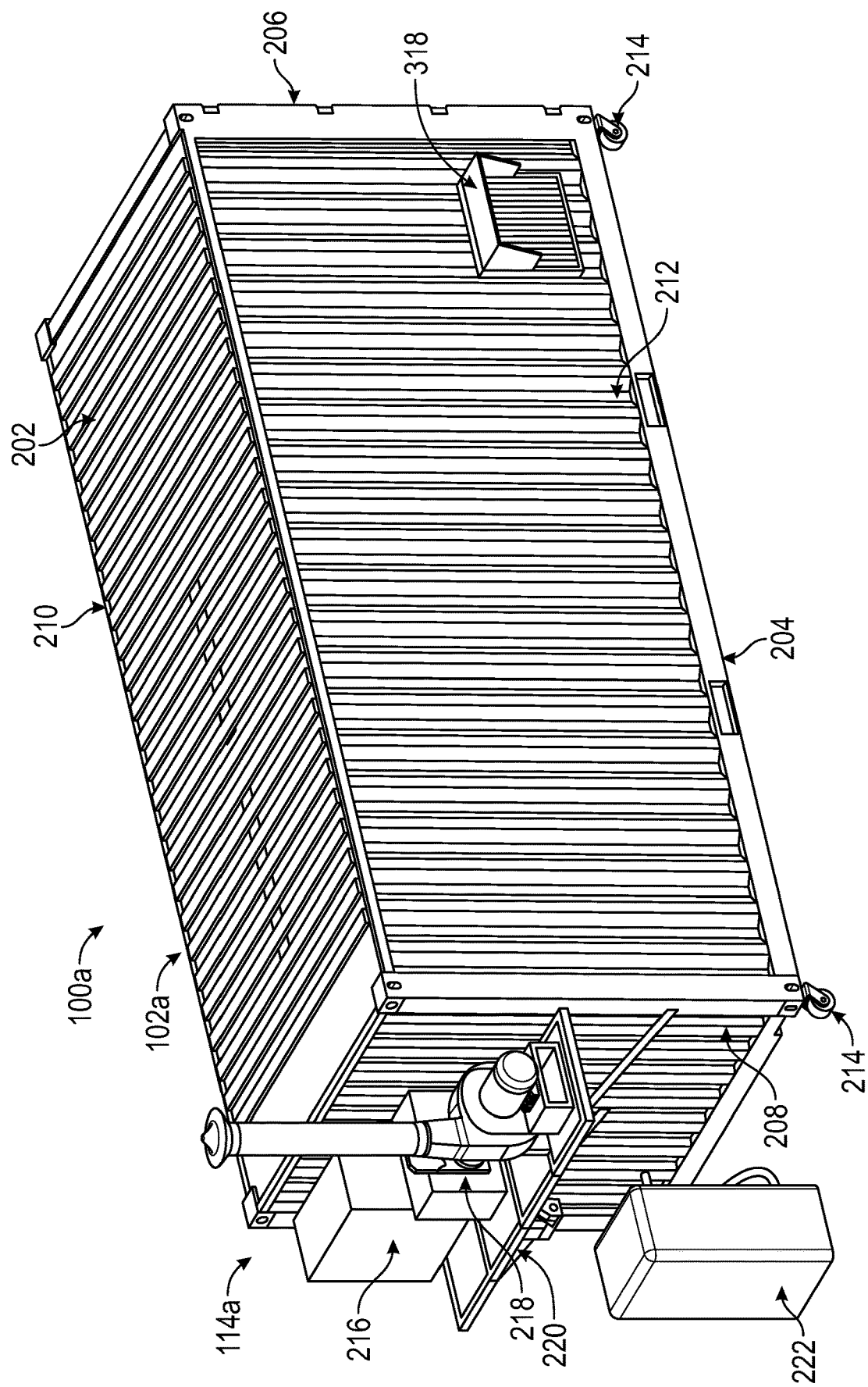
FIG. 2 is a rear perspective view of an example embodiment of a system consistent with the present disclosure.
Figure 3:
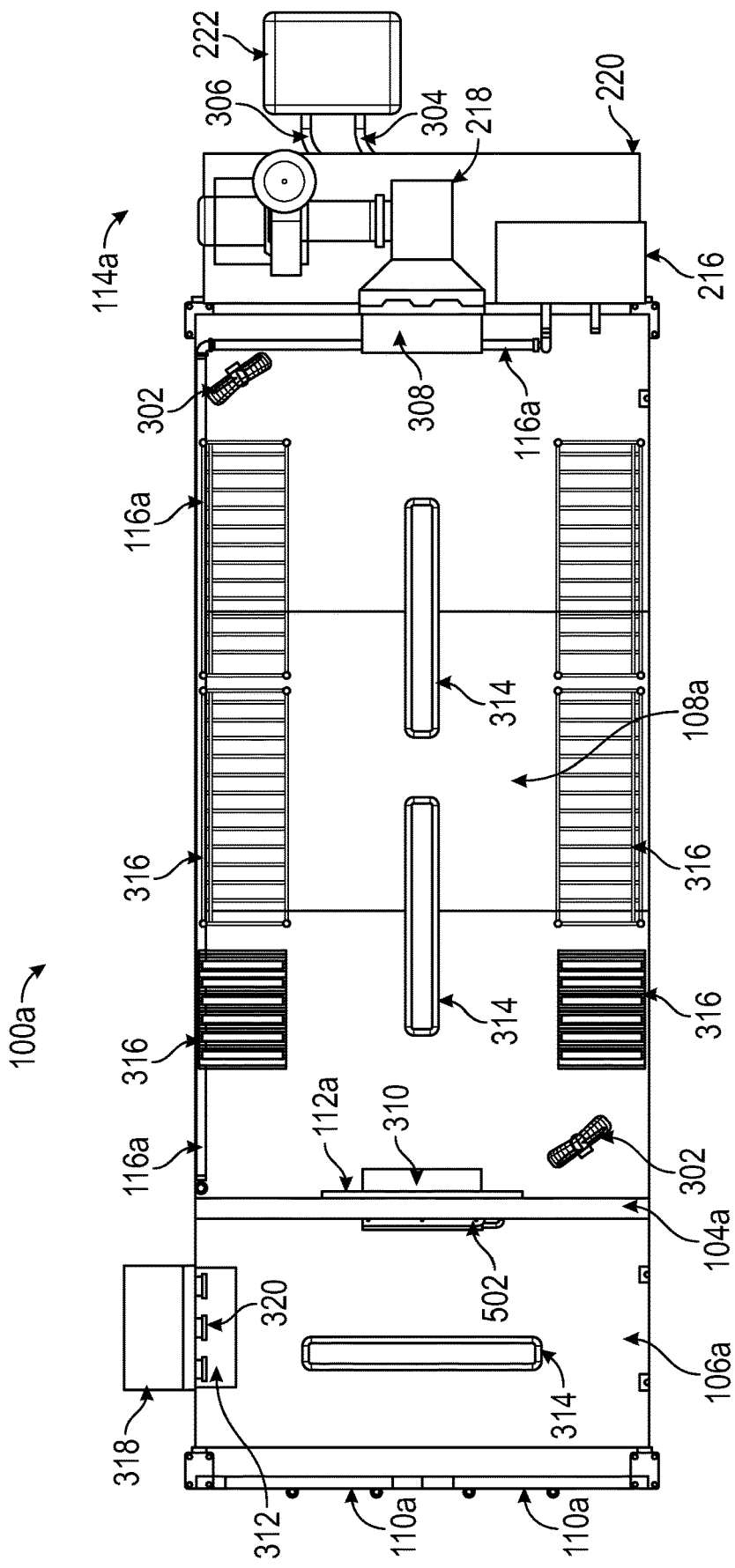
FIG. 3 is a top cut-away plan view of the system shown in FIG. 2.
Figure 4:
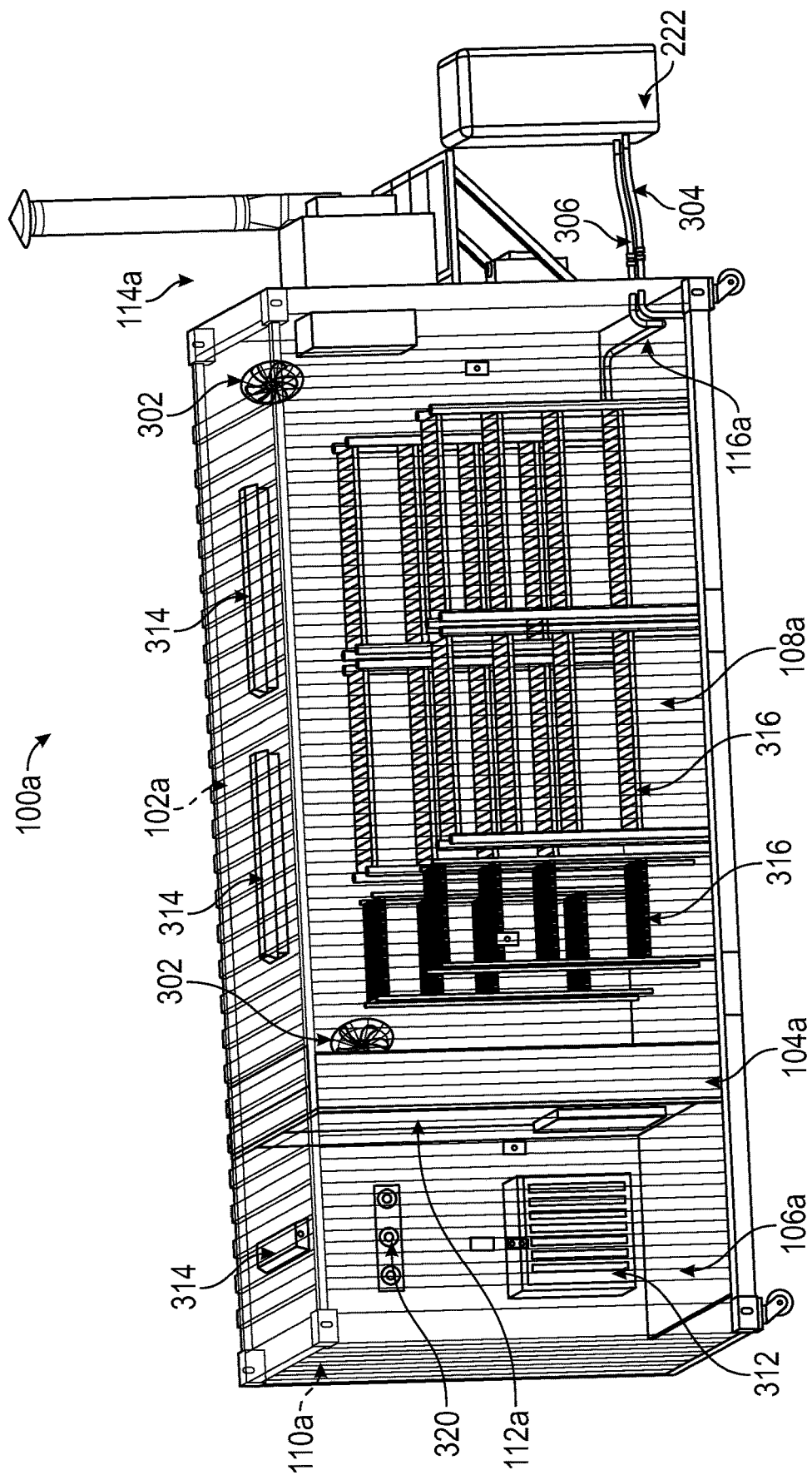
FIG. 4 is a side perspective view of the system shown in FIG. 2 with portions shown in ghost to illustrate interior components.

Turning now to FIGS. 2-4, there is illustrated one example embodiment 100a of a system consistent with the present disclosure configured for operation using a vaporized decontaminant, such as HPV. The illustrated embodiment 100a includes a portable enclosure 102a with a partition 104a therein to define an anteroom 106a and a decontamination chamber 108a. One or more entry doors 110a allow access to the anteroom 106a and one or more decontamination chamber doors 112a allow entry from the anteroom 106a into the decontamination chamber 108a. A decontaminant generator system 114a is provided at the outside of the enclosure 102a for causing a decontaminant to emanate from one or more decontaminant distributors 116a in the decontamination chamber 108a. An optional air agitation system 118 including one or more electric fans 302 may be provided in the decontamination chamber 108a, e.g., in opposing corners, for agitating the air and the decontaminant within the decontamination chamber 108a.

In the illustrated example embodiment, the enclosure 102a is formed from rigid top 202, bottom 204, front 206, back 208 and side 210, 212 walls. The front wall 206 may be at least partially defined by the entry doors 110a. In some embodiments, the enclosure 102a may constructed from a known shipping container, e.g., a 20' Conex shipping container and the partition 104a may be positioned at about five feet inward from the front wall 206. The enclosure 102a may also have a plurality of wheels 214 on the bottom thereof, e.g., at each corner of the enclosure, to allow easy maneuvering of the enclosure 102a for transporting and positioning the enclosure 102a in a desired location.

The decontaminator generator system 114a includes an electrical box 216 for coupling to an electrical power source, e.g., 120 v line or generator voltage, for distributing electrical power to electrical components of the system 100a. The electrical box 216 may also include a controller for controlling decontamination and degassing, e.g., according to computer readable instructions, and a user interface for providing user input/output to the controller. The decontaminator generator system 114a may also include blower and ductwork 218 for creating airflow in the enclosure 102a, a support platform 220 for supporting the blower and ductwork 218, and a decontaminant generator 222 for generating vaporized decontaminant.

The decontaminant generator 222 may be coupled to the decontaminant distributor 116a, which may be configured as piping positioned along the top and/or side walls, e.g., along the entire length of the side walls, of the decontamination chamber 108a. The piping forming the decontaminant distributor 116a may have having holes therein for distributing the decontaminant in the decontamination chamber 108a. The piping may return to the decontaminant generator 222 to recycle unused decontaminant back to the decontamination chamber 108a.

In some embodiments, the decontaminant generator 222 may be removably coupled to the decontaminant distributor 116a. For example, the decontaminant generator 222 may be coupled to the decontaminant distributor by first 304 and second 306 hoses that are removably attached, e.g., using known quick connect hose connectors, to the piping forming the decontaminant distributor 116a at the outside of the enclosure 102a. This allows facile disconnection of the decontaminant generator 222 from decontaminant distributor 116a of one enclosure 102a and connection of the decontaminant generator 222 to the decontaminant distributor 116a of another disclosure 102a.

At locations where air ingress/egress from the anteroom 106a and decontamination chamber 108a is desired, e.g., for degassing the decontaminant from the enclosure, openings may be provided in the enclosure and the openings may be covered by associated filters, e.g., high-efficiency particulate air (HEPA) filters. As shown in FIG. 3, for example, a HEPA filter 308 may be provided in an opening of the enclosure 102a for coupling to the blower and ductwork 218 of the decontaminant generator system 114a to the decontamination chamber 108a, a HEPA filter 310 may be coupled in an opening in the decontamination chamber door 112a, and a HEPA filter 312 may be provided in an opening formed in the side wall 212 of the anteroom 106a. A rain hood 318 may be installed at the exterior of the enclosure 102a over the top of opening in the side wall 212 in which the HEPA filter 312 is placed to prevent rain or snow from interfering with the filter 312.

The decontamination chamber 108a and the anteroom 106a may also be provided with lighting fixtures 314 and shelving 316 for storing patient care equipment. The floor of the decontamination chamber may be provided with a covering, e.g., a diamond tread plate covering, to protect the decontaminant from absorbing into the floor. Pressure gauges 320 may be mounted on the interior wall of the anteroom 106a for monitoring the pressure inside the anteroom 106a, inside the decontamination chamber 108a and/or the pressure at the exterior of the enclosure 102a.

Figure 5:
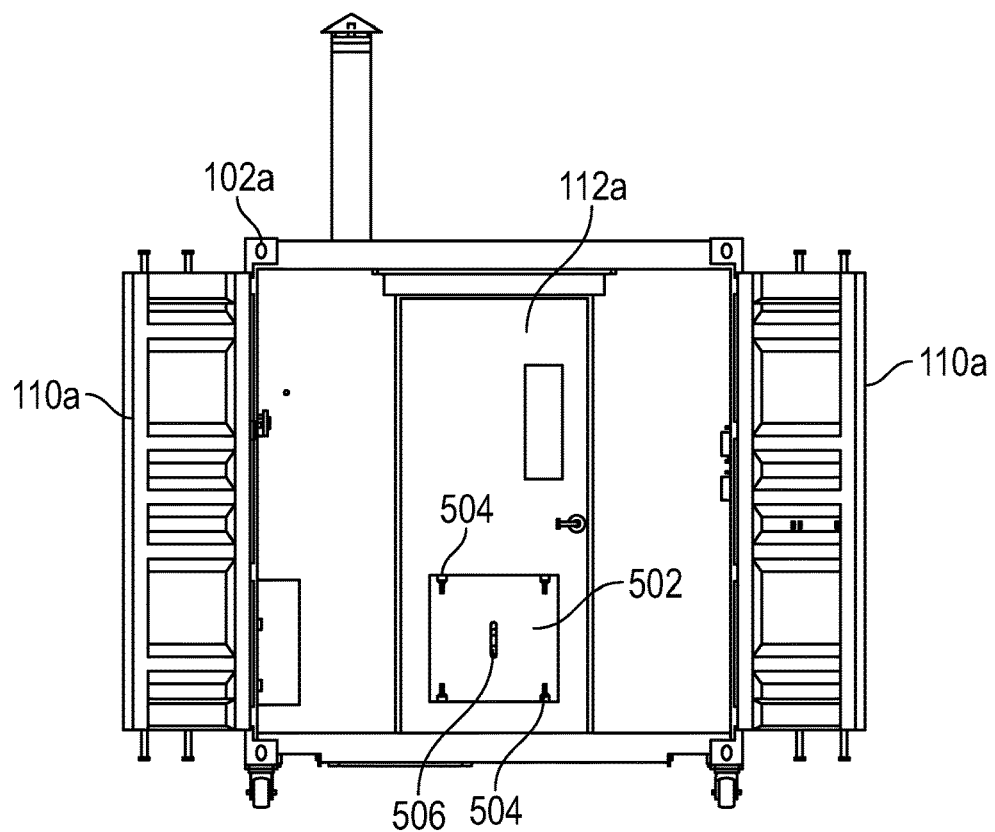
FIG. 5 is a front view of the system shown in FIG. 2 with entry doors open and one example of a cover installed on a door filter.
Figure 6:
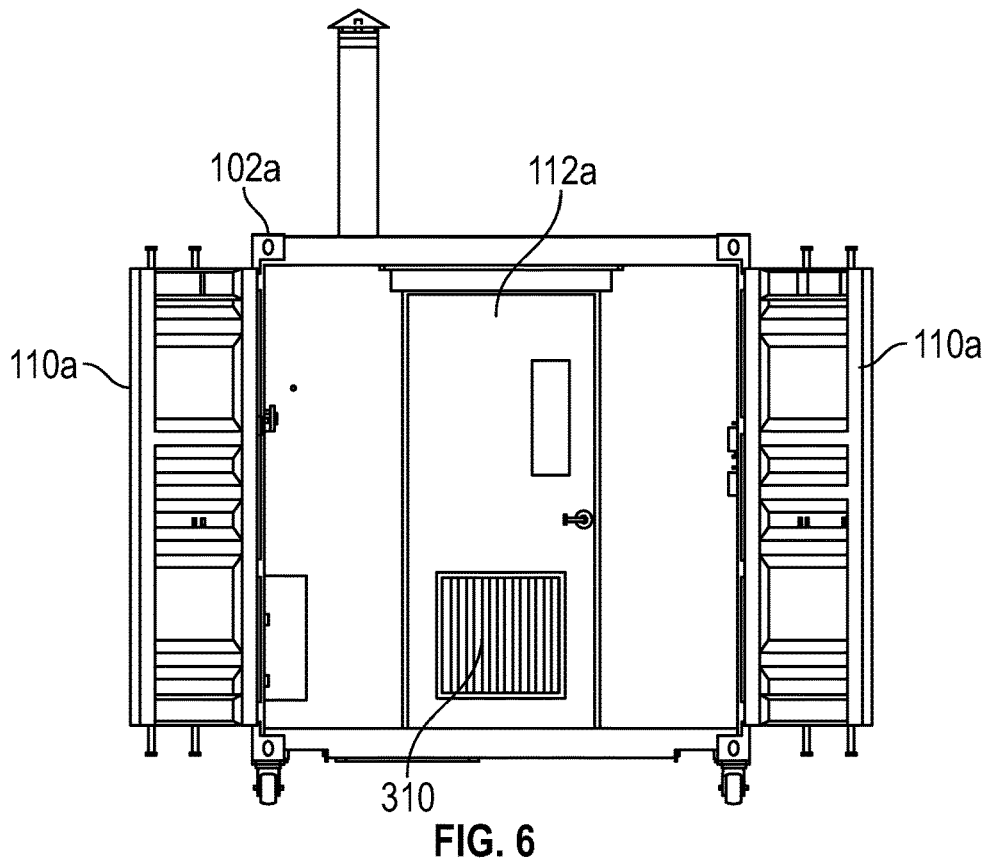
FIG. 6 is a front view of the system shown in FIG. 2 with entry doors open.

As shown in FIGS. 5, the HEPA filter 310 in the decontamination chamber door 112a may be blocked by a cover 502 to seal the decontamination chamber 108a during decontamination. In the example embodiment shown in FIG. 5 the cover 502 includes four latches 504, i.e., one at each corner of the cover 502, for latching the cover 502 onto the portion of the door 112a housing the HEPA filter 310 and a handle 506 to facilitate attachment and removal of the cover 502. The cover 502 may be removed to expose the HEPA filter 310 during degassing, as shown in FIG. 6.

Figure 7:
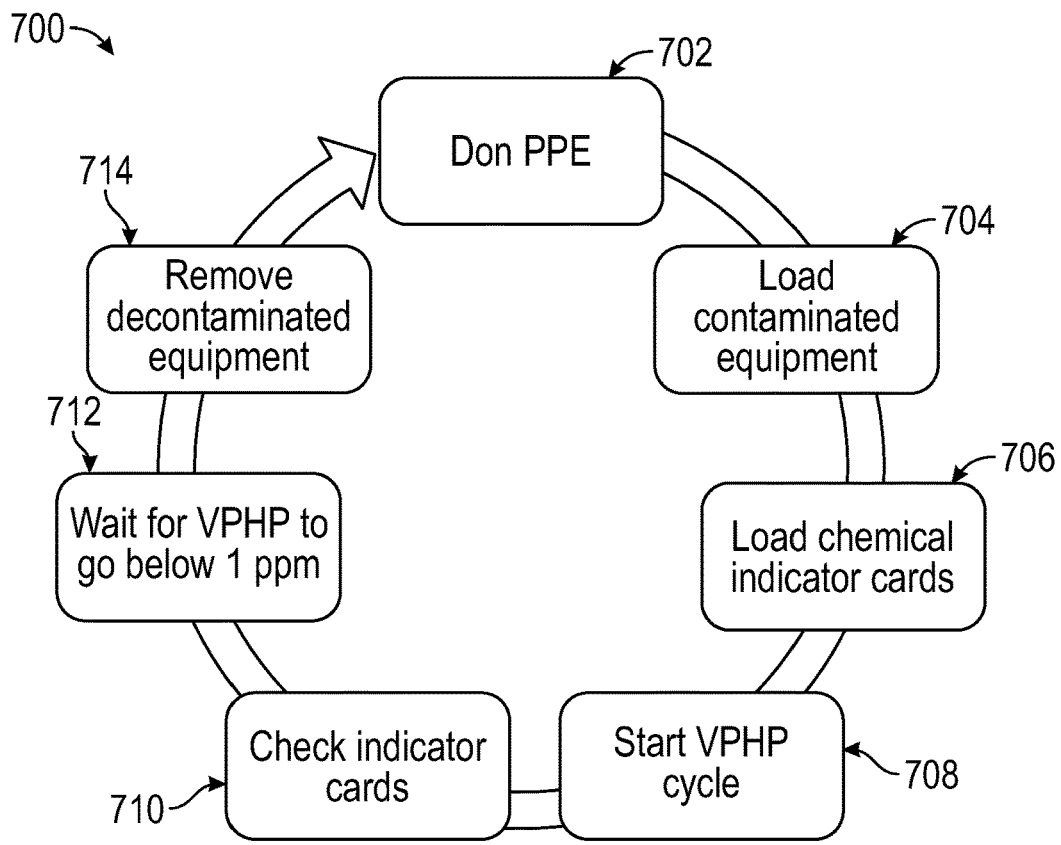
FIG. 7 is a block flow diagram illustrating operations according to a method consistent with the present disclosure.

FIG. 7 is a block flow diagram illustrating one example method 700 of operating a system consistent with the present disclosure, e.g., system 100a. In the illustrated example, the operator dons PPE 702 per any required facility protocol. The operator them opens decontamination chamber door 112a and loads potentially contaminated equipment 704, e.g., onto shelves 316 or hangers ensuring the equipment does not touch each other. Once the decontamination chamber 108a is loaded, one or more chemical indicator (CI) cards may be loaded or placed 706 in the chamber 108a. A variety of CI cards are known. For example, the CI cards may be Bioquell TD078-700 chemical indicator cards commercially available from Bioquell, Inc. of Horsham, Pa., USA, or the equivalent thereof. In some embodiments, three to five CI cards may be placed in the chamber. The CI cards provide visual evidence of effective decontamination.

After the CI cards are placed in the chamber, the door 112a is closed and latched and the cover 502 is latched to the door over the HEPA filter 310. The operator then starts a decontamination cycle 708 using controls in the anteroom 106a or on the decontaminant generator system 114a. In some embodiments, an optional hand-held peroxide monitor may be used to confirm safe H2O2 levels outside of the chamber. Upon completion of the decontamination cycle, the operator may visually check the CI card(s) 710 to ensure a desired level decontamination, e.g., a 6-log reduction, has been achieved. The cover 502 may then be removed from the door 112a and the decontaminant generator system 114a may be operated to aerate the decontamination chamber 108a and, e.g., until a peroxide concentration is reduced to below 1 ppm 712. Catalytic carbon filters may be used to filter peroxide in the decontamination chamber 108a. Finally, the decontaminated equipment is removed 714 from the decontamination chamber 108a and distributed for reuse.

Figure 8:
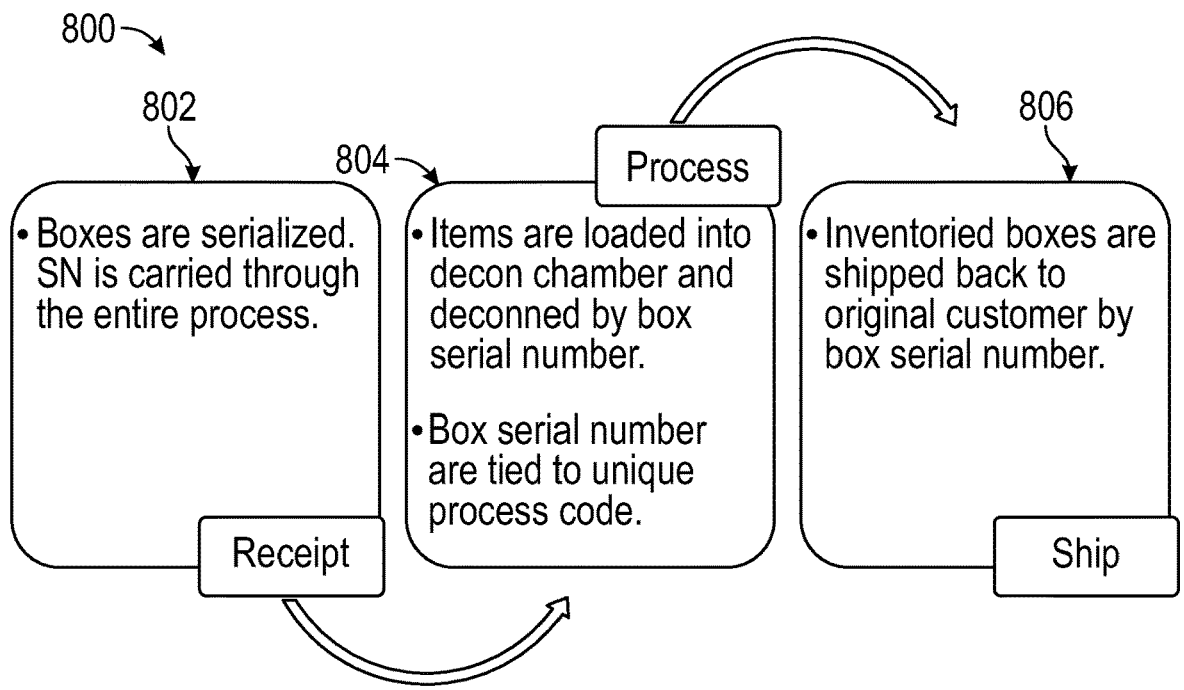
FIG. 8 is a block flow diagram illustrating operations according to a method consistent with the present disclosure.

In some embodiments of a method consistent with the present disclosure, the system may be used by receiving patient care equipment from a hospital or healthcare setting, processing the patient care equipment to decontaminate the equipment, and then shipping the equipment back to the hospital. FIG. 8, for example, is a block flow diagram illustrating one example of a method 800 consistent with the present disclosure. In the illustrated embodiment, a receiving operation 802 includes collecting boxes of patient care equipment, e.g., N95 mask, from a hospital or other healthcare institution, and giving the boxes a serial number. In a processing operation 804 the items in the boxes are loaded into a system consistent with the present disclosure, e.g., in an enclosure 102a, and decontaminated by box serial number, which are tied to a process code. In some embodiments, each item in a box may be marked to identify the number of times the item has been decontaminated to facilitate requirements regarding the number of times an item may be decontaminated. In a shipping operation 806 the inventoried boxes are shipped back to the hospital or institution from where they came from using the box serial number.

In some embodiments, a box serial number for each box may be assigned to the box from a database of serial numbers, and a label bearing the serial number is generated and applied to each box. Data including the date received, receiver name, Site/location code, number of boxes and type of items in the box may be stored in the database in a record associated with the serial number. A chain of custody (COC) label may also be printed with the same box serial number for signed COC.

In some embodiments of the processing operation 804, the database may be configured to generate a unique process code for decontaminating each batch. All box serial numbers loaded into the decontamination chamber 108a are linked to this process code for traceability. To decontaminate, the box serial number may be scanned and the boxes unpacked, and the items therein loaded in the decontamination chamber 108a, e.g., onto shelves 316 and as described above in connection with FIG. 7. A small placard or other identifier may be provided on a placard attached to each shelf to identify the Site/Location code of the box being unpacked for the items on that shelf. Once the decontamination chamber 108a is full, a decontamination process consistent with the present disclosure may be initiated, e.g., as described in connection with FIG. 7. During decontamination, information such as lot numbers, test values, etc. that pertain to the process may be recorded and tied to the process code. Boxes for shipping may also be assembled during this time.

After the decontamination process is complete, processing is complete and checks have been made, box serial numbers for boxes that were loaded into the decontamination chamber 108a are printed. These are the same box serial numbers that were assigned when originally received. The shelves 316 are unloaded one according to the Site/Location code. Each item may be marked or labeled with green dot labels to indicate they have been decontaminated. The items are counted/inventoried to record the quantities as they are packed into the corresponding box.

In some embodiments of the shipping operation 806, the box serial numbers are scanned to record the items being shipped. The shipment will then have complete list of items (quantities and type). A packing list containing box serial numbers and equipment item totals may be printed for a courier to sign.

While FIGS. 7 and 8 illustrate various operations according to example embodiments consistent with the present disclosure, it is to be understood that not all of the operations depicted or described in connection with FIGS. 7 and 8 are necessary for other embodiments. Indeed, it is fully contemplated herein that in other embodiments of the present disclosure, the operations depicted or described in connection with FIGS. 7 and 8, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

A system and method consistent with the present disclosure may decontaminate any type of patient care equipment to an acceptable level so that equipment can be re-used by healthcare professionals during a period when the availability of equipment is limited. For example, some embodiments of a system 100 consistent with the present disclosure have been found effective in decontaminating 80,0000, N95 mask per day to achieve 99.9999% sterilization up to 20 times without degrading performance of the mask. In other embodiments, approximately 2,000 face shields may be decontaminated per day in a single decontamination chamber consistent with the present disclosure. The process parameters may vary depending on the size of the enclosure 120a, the configuration of the decontaminant generator system, etc. In some embodiments using a system 100a as shown and described in connection with FIGS. 2-6, each decontamination cycle in the system may include: injecting HPV into the decontamination chamber until, for example, achieving a saturated atmosphere indicated by micro condensation; maintaining the HPV exposure for a 150-minute dwell time, for example, and allowing the HPV to off gas to a level of 1 ppm, for example, prior to post decontamination processing. In some embodiments, a minimum of five calibrated known chemical indicators are dispersed throughout the system to indicate a successful decontamination cycle.

A system 100 and method consistent with the present disclosure may be implemented in a variety of form factors and configurations. In some embodiments, the system may be configured as a mobile appliance intended for indoor use, e.g., at medical facilities. The system may include an enclosure defining a decontamination chamber, e.g., without an anteroom, a decontaminant distributor and a decontaminant generator system. In some embodiments, for example, the system may be a wheeled, e.g., refrigerator-sized, appliance that can pass through doorways, plug into standard 120V power outlets, and be immediately ready to decontaminate patient care equipment such as Personal Protective Equipment (PPE). The convenient form factor may allow for reliable decontamination with little user training and few consumables.

Figure 9:
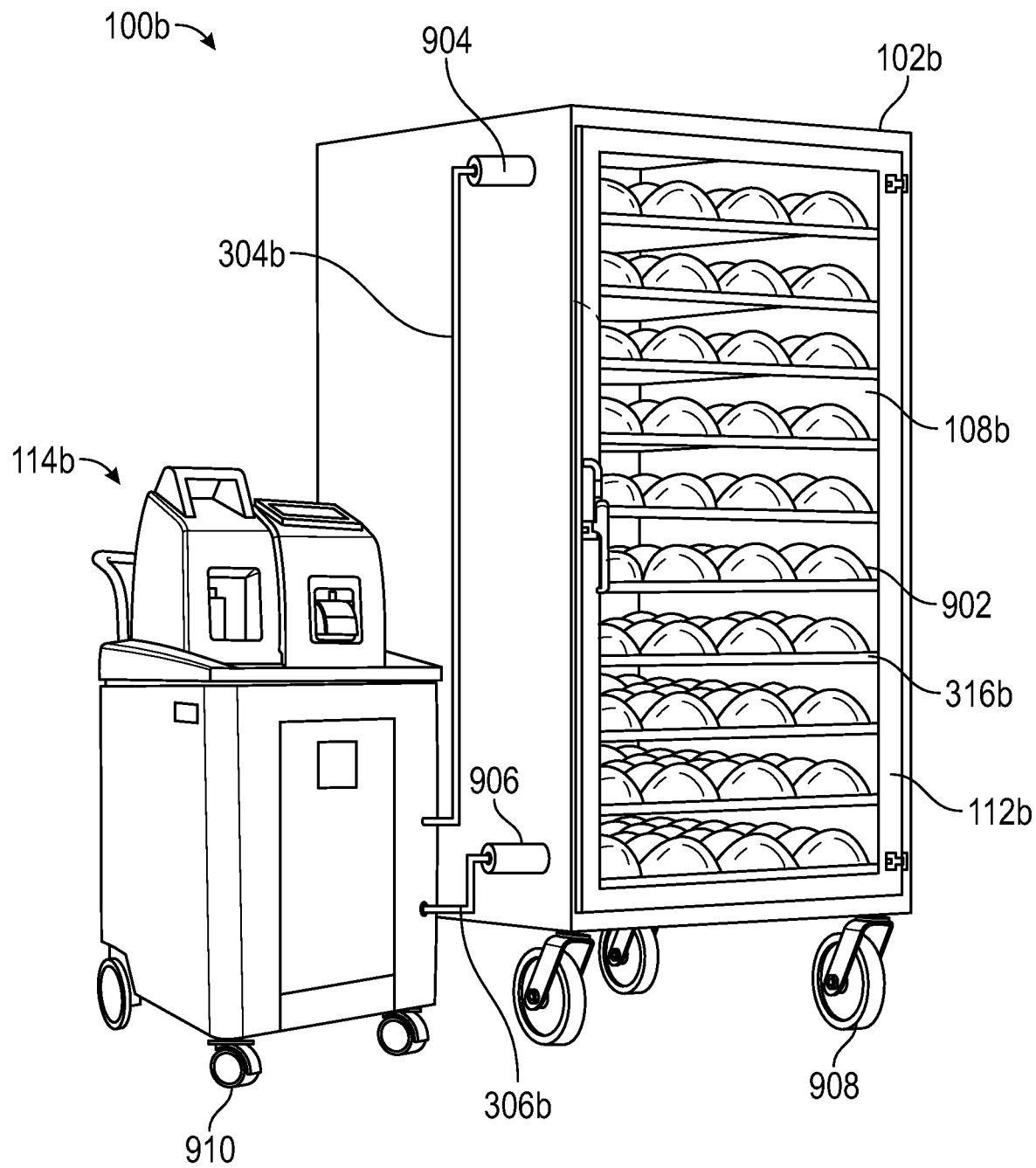
FIG. 9 is perspective view of another example embodiment of a system consistent with the present disclosure.

FIG. 9 illustrates one example of a system 100b consistent with the present disclosure configured as a mobile system and including an enclosure 102b mounted on wheels 908 and defining a decontamination chamber 108b, and a decontaminant generator system 114b mounted on wheels 910. In some embodiments the decontaminant generator system 114a may be a Bioquell L-4 VPHP generator commercially available from Bioquell, Inc. of Horsham, Pa., USA. The system may be powered by plugging in to a standard 120VAC wall outlet.

The enclosure 102b may be configured as a sealed cabinet with a glass entry door 112b. The enclosure 102b may support shelving or racks 316b for supporting patient care equipment shown as N95 mask 902 in the illustrated example embodiment. In some embodiments, enclosure 102b may be about 30"×48"×36" in dimension.

The enclosure 102b has a first port 904 and a second port 906. The ports 904 and 906 extend from the decontamination chamber 108a to the exterior of the enclosure 102b and may be coupled to associated first and second hoses 304b, 306b. HPV delivered by the decontaminant generator system 114b will flow into the decontamination chamber 108b through the first hose 304b and the first port 904, and once a decontamination cycle is complete the HPV will be withdrawn from the decontamination chamber 108b by the decontaminant generator system 114b through the second hose 306b and the second port 906. The decontaminant generator system 114b supplies and maintains HPV at the proper concentrations. At the end of the HPV decontamination cycle, the decontaminant generator system 114a can safely lower the HPV concentration through the second port 906 and the second hose 306b and the without additional ventilation. Alternatively, the system 100b can vent the HPV from the decontamination chamber outdoors via a lab hood or dedicated duct to speed the process.

To set up the system 100b, the enclosure 102b and decontaminant generator system 114b are wheeled into a designated room. In some embodiments, the chamber may be provided at a point of care for collecting PPE and then wheeled to a designated room. Before movement, the exterior of the enclosure 102b may be disinfected, e.g., wiped with 70% ethanol.

The decontaminant generator system 114b may be plugged into a standard 120 V outlet. The two hoses 304b, 306b may be connected between the ports 904, 906, respectively, of the enclosure 102a and decontaminant generator system 114b using standard fittings. In some embodiments, a commercially available 5 L bottle of 35% H2O2 is loaded into the decontaminant generator system 114b and will last approximately 20 decontamination cycles before it must be replaced. The system may be operated generally as described above in connection with FIG. 7.

In some embodiments, a single decontaminant generator system 114b may be used with multiple chambers 102b. In a system with four chambers 102b, for example, up to 1,000 N95 respirators 902 may be decontaminated in a single day with a low logistical footprint. The chamber(s) 102b may be reconfigurable to allow different types of patient care equipment, e.g., PPE, to be supported in the enclosure 102b in a way that maximizes contact of the equipment with decontaminant, e.g., HPV, in the enclosure 102b to achieve a desired level of decontamination.

In embodiments of systems consistent with the present disclosure wherein the decontaminant is a spray or vapor, such as a hydrogen peroxide vapor (HPV), that wets the patient care equipment, or wherein the patient care equipment is otherwise wet after decontamination, the patient care equipment may be dried by allowing dry air to passively flow around the patient care equipment or by actively forcing dry air to flow around the patient care equipment. To decrease drying time and increase throughput in such embodiments, the patient care equipment may be supported on racks configured to receive pressurized dry air and direct the pressurized dry air toward the patient care equipment supported thereon. These rack configurations may be provided, for example, in place of shelves 316, 316b in the systems 100a, 100b.

Figure 10:
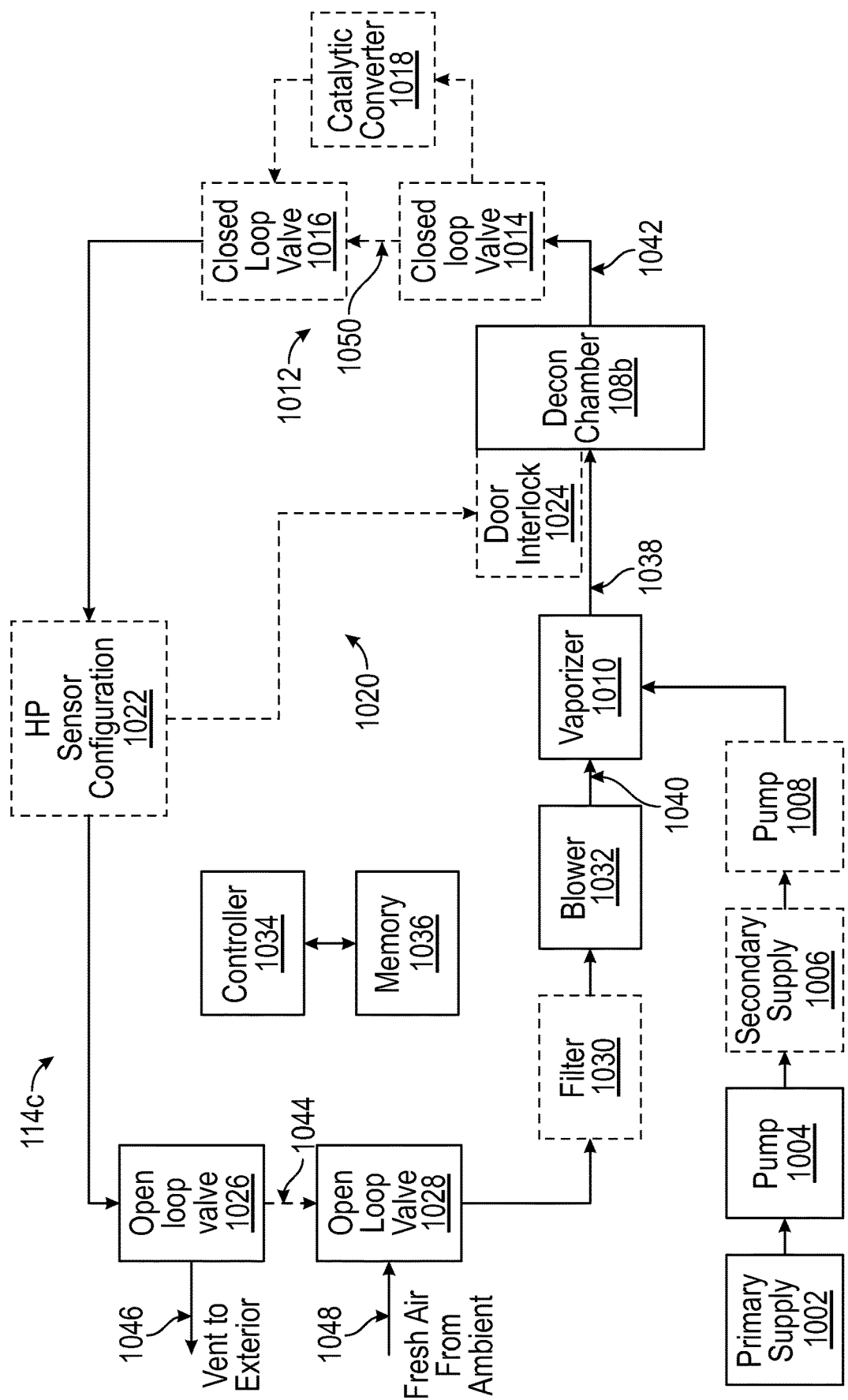
FIG. 10 is a block diagram of another example embodiment of a system consistent with the present disclosure.

A decontaminant generator system 114 useful in connection with a system 100b may be provided in a variety of configurations. FIG. 10, for example, illustrates another embodiment of a decontaminant generator system 114c coupled to a decontamination chamber 108b. In the illustrated example embodiment, the decontaminant generator system 114c includes: a primary supply 1002 of hydrogen peroxide solution 1002; a first pump 1004; an optional secondary supply of hydrogen peroxide solution 1006; an optional second pump 1008; a vaporizer 1010; an optional converter configuration 1012 including a first closed loop valve 1014, a second closed loop valve 1016 and a catalytic converter 1018; an optional door interlock configuration 1020 including an optional hydrogen peroxide (HP) sensor configuration 1022 and an optional door interlock 1024; a first open loop valve 1026; a second open loop valve 1028; an optional filter 1030 and a blower 1032. The system also includes a controller 1034 coupled to the components of the system for controlling operation of the components, e.g., in response to outputs from various sensors (not shown) and/or in response to computer readable instructions stored in a non-transient memory 1036. For clarity and ease of illustration, the connections between the controller 1034 and the system components and sensors are not shown. Also, although the example embodiment 114c shown in FIG. 10 will be described herein in connection with the decontamination chamber 108b, the illustrated configuration may be used in with any enclosure 102 and decontamination chamber 108 consistent with the present disclosure.

In general, in the illustrated decontaminant generator system 114c the system components are operatively coupled for configuration in a closed loop configuration during a decontamination cycle and for decontaminating patient care equipment in the decontamination chamber 108b and also for configuration in an open loop configuration and for degassing the decontamination chamber 108b to remove HPV from the decontamination chamber 108b after a decontamination cycle. In the closed loop configuration, a hydrogen peroxide solution is stored in the primary supply 1002 and pumped from the primary supply 1002 by the pump 1004. The primary supply 1002 may be configured as a tank that can removably attach to the pump for replacement when the tank is empty. A level sensor may monitor the level of the hydrogen peroxide the primary supply 1002 and trigger a level alarm when the level is low to indicate replacement of the primary supply 1002 is necessary or suggested. The hydrogen peroxide solution may be any known solution for generating HPV and, in some embodiments, may be a solution of about 35% hydrogen peroxide and 65% water.

The pump 1004 may pump the hydrogen peroxide solution from the primary supply 1002 directly to the vaporizer 1010, or to the secondary supply 1006. The secondary supply 1006 may also be in the form of a tank and the pump 1004 may be configured for pumping hydrogen peroxide from the primary supply 1002 to the secondary supply 1006. With this configuration, hydrogen peroxide from the secondary supply 1006 can be used for a decontamination cycle while the primary supply 1002 is replaced. This can ensure that a supply of hydrogen peroxide is consistently available during decontamination.

In some embodiments, a level sensor may monitor the amount of hydrogen peroxide solution in the secondary supply 1006. The controller 1034 may be configured to turn the pump 1004 on or off in response to the output of the level sensor. For example, the controller 1032 may turn the pump 1004 on when the level sensor indicates the level of hydrogen peroxide in the secondary supply is low and may turn the pump 1004 off when the level sensor indicates the level of hydrogen peroxide in the secondary supply is high. If the level sensor associated with the primary supply 1002 and the level sensor associated with the secondary supply 1006 both indicate a low level of hydrogen peroxide, the controller 1034 may be configured to discontinue decontamination.

The pump 1008 is configured to pump hydrogen peroxide from the secondary supply 1006 to the vaporizer 1010. In some embodiments, the controller 1034 may be configured to turn the pump on or off in response to sensors associated with the vaporizer 1010. For example, the controller 1032 may be configured to turn the pump 1008 on when a decontamination cycle is initiated, when one or more temperature sensors indicate that the vaporizer 1010 has reached the temperature required to vaporize the hydrogen peroxide, and/or when a level sensor indicates that a fluid level within the vaporizer 1010 is low.

The vaporizer may take a variety of configurations and generally includes one or more heating elements to vaporize the hydrogen peroxide solution provided by the pump 1008 or the pump 1004. The blower 1032 may be known blower configuration for providing a positive air pressure to move the vaporized hydrogen peroxide from the vaporizer 1010 to the decontamination chamber 108b. The conduit 1038 between the vaporizer and the decontamination chamber may be connected to the decontamination chamber 108b, e.g., at port 904 (FIG. 9), and/or the vaporizer 1010 using quick connect/disconnect connectors to enable facile connection of the decontaminant generator system 114c to the decontamination chamber 108b. The conduit 1038 may be heated, e.g., using heat trace elements, to ensure the vaporized hydrogen peroxide does not condense prior to reaching the decontamination chamber. The conduit 1040 from the blower 1032 to the vaporizer 1010 may also be heated to ensure the pressurized air from the blower 1032 is not cool enough to condense the vaporized hydrogen peroxide.

The HPV introduced into the decontamination chamber 108b may be recycled to the vaporizer 1010 through an output conduit 1042 from the decontamination chamber 108b, e.g., coupled to port 906 (FIG. 9). In the closed loop configuration, the open loop valve 1026 is configured to allow flow along the path 1044 and block a venting path 1046 to the exterior, and the open loop valve 1028 is configured to pass flow from the path 1044 and block a fresh air path 1048. The blower 1032 draws HPV from the decontamination chamber 108b through the output conduit 1042, through the optional HP sensor configuration 1022, through the optional door interlock configuration 1020, through the path 1044 between the open loop valves 1026 and 1028 and back to the blower 1032 through the optional filter 1030. The optional filter 1030 may be, for example, a high efficiency particular air (HEPA) filter configured to filter contaminants from the recycled HPV. The blower 1032 directs the recycled HPV to the vaporizer 1010 to move the recycled HPV and additional HPV from the vaporizer 1010 into the decontamination chamber 108b.

The optional door interlock configuration 1020 may thus prevent the door to the decontamination chamber 108b from opening when there are dangerous levels of hydrogen peroxide in the decontamination chamber 108b. In particular, the HP sensor configuration 1022 may sense the level of hydrogen peroxide in the recycled HPV. The door interlock 1024 may be responsive to the output(s) of the HP sensor configuration 1022 and may be configured to lock the door, e.g., door 112b (FIG. 9), to the decontamination chamber 108b if the level of hydrogen peroxide in the recycled HPV is above a threshold and to allow the door open if the level of hydrogen peroxide in the recycled HPV is below a threshold. In some embodiments, the threshold may be 1 part-per-million (ppm). The door interlock 1024 may take a known configuration. In some embodiments, for example, the door interlock 1024 may include a solenoid lock responsive to the output of the HP sensor configuration 1022, e.g., directly or via a control signal from the controller 1034.

A variety of configurations for the HP sensor configuration 1022 may be implemented in a system consistent with the present disclosure. In some embodiments, the HP sensor configuration 1022 may be a single hydrogen peroxide sensor configured to sense the range of expected hydrogen peroxide levels in the recycled HPV. In other embodiments, the HP sensor configuration 1022 may include a high-level HP sensor and a low-level HP sensor. When the hydrogen peroxide level sensed by the high-level HP sensor drops to a value within the range of the low-level sensor, the low-level sensor may be connected in a parallel path with the high-level sensor to sense the hydrogen peroxide in the recycled HPV. The connection/disconnection of the parallel paths between the high-level sensor and the low-level sensor may be implemented using valves controllable by the controller in response to the output of the high-level sensor.

In the open loop configuration for degassing the decontamination chamber 108b, the open loop valve 1026 is configured to block flow along the path 1044 and open a venting path 1046 to the exterior, and the open loop valve 1028 is configured to block flow from the path 1044 and open a fresh air path 1048. Also, in the open loop configuration, the pump 1004 and the pump 1008 are disabled and the vaporizer 1010 acts only to pass air from the blower 1032 to the decontamination chamber 108b. The blower 1032 draws fresh air through the path 1048 coupled to the open loop valve 1028 and optionally through the filter 1032 and moves the fresh air through the vaporizer 1010 and into the decontamination chamber 108b through the conduit 1038. The introduction of fresh air into the decontamination chamber 108b forces HPV out of the decontamination chamber 108b through the conduit 1042, through the optional converter configuration 1012, through the optional HP sensor configuration 1022, through the open loop valve 1026 and out to the exterior through the path 1046.

In embodiments including the optional converter configuration 1012, during decontamination in closed loop configuration flow through the catalytic converter 1018 is blocked. In particular, the closed loop valve 1014 is configured to allow flow along the path 1050 and block a path to the catalytic converter 1018, and the closed loop valve 1016 is configured to pass flow from the path 1050 and block a path from the catalytic converter 1018. In an open loop configuration for degassing the decontamination chamber 108b, flow from the decontamination chamber 108b is passed through the catalytic converter 1018. In particular, the closed loop valve 1014 is configured to block flow along the path 1050 and open a path to the catalytic converter 1018, and the closed loop valve 1016 is configured to block flow from the path 1050 and open a path from the catalytic converter 1018. The catalytic converter may take a known configuration for converting the HPV from the decontamination chamber, e.g., into water. One example of a catalytic converter 1018 is the Bioquell R-30 catalytic converter commercially available from Bioquell, Inc. of Horsham, Pennsylvania, USA.

Figure 11:
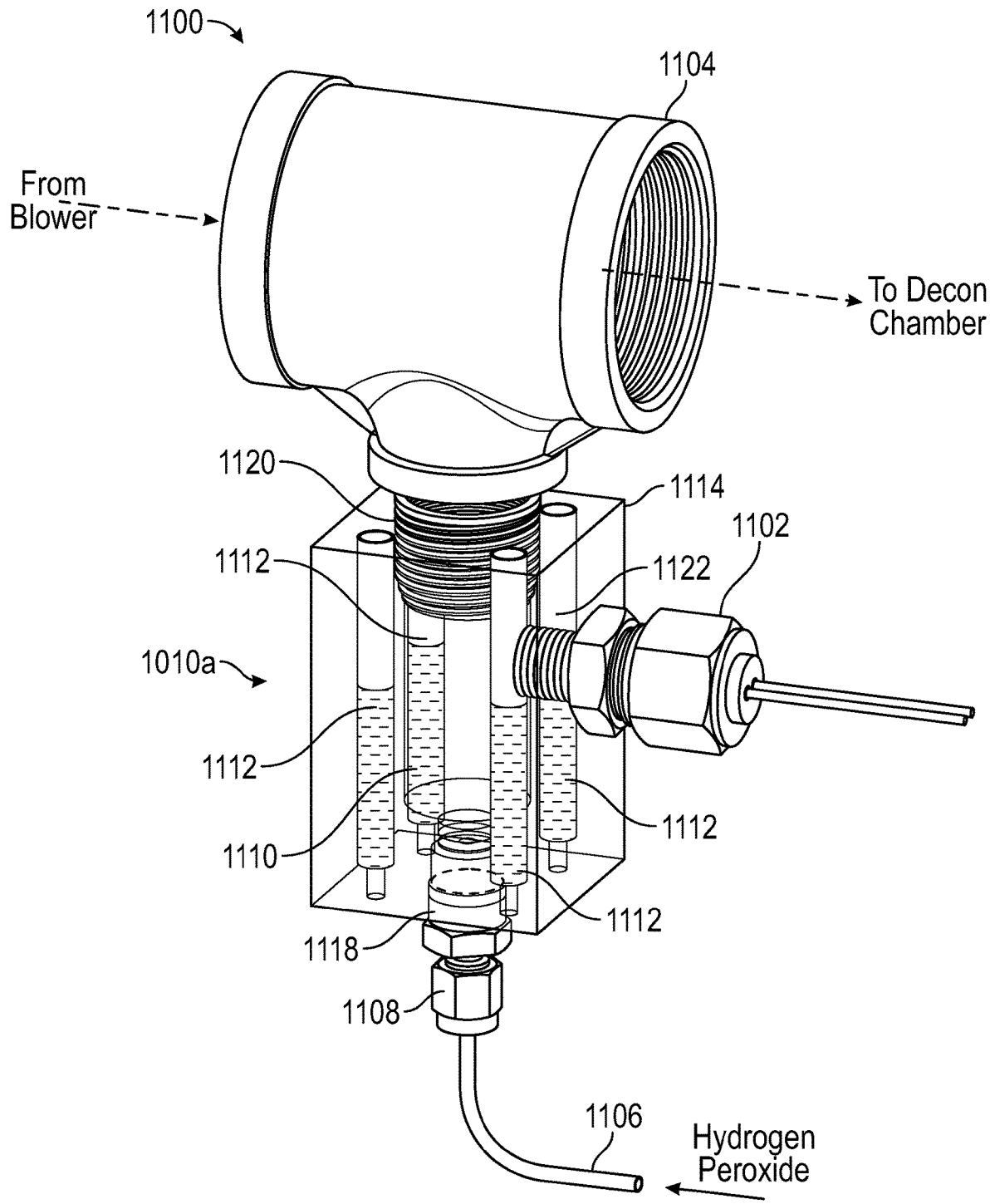
FIG. 11 is a perspective, partial ghost view of one example of a vaporizer configuration consistent with the present disclosure.
Figure 12:
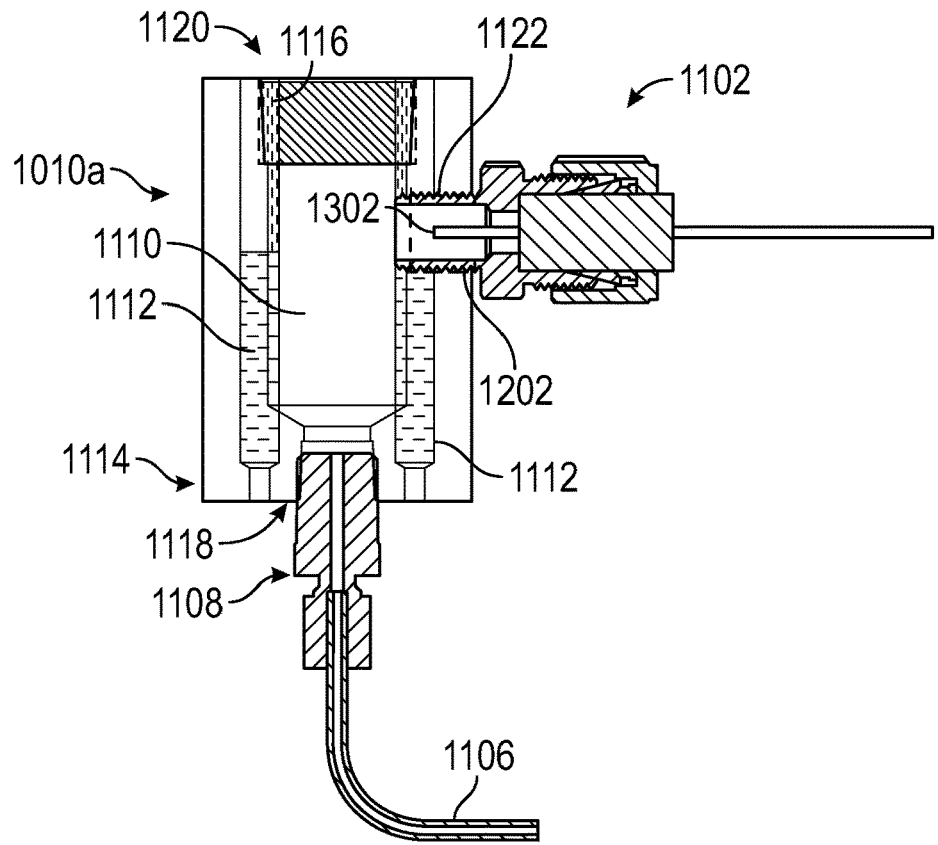
FIG. 12 is a side sectional view of a portion of the vaporizer configuration shown in FIG. 11.
Figure 13:
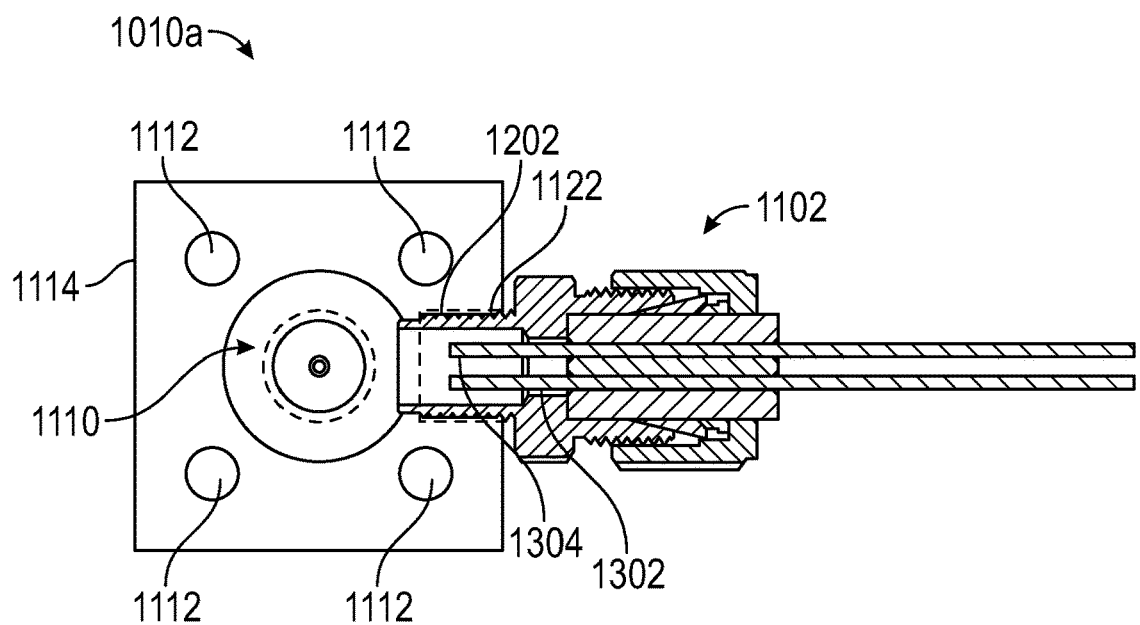
FIG. 13 is a top sectional view of a portion of the vaporizer configuration shown in FIG. 11.

The vaporizer 1010 acts as a decontaminant generator and may take a variety of configurations. FIGS. 11-13 illustrate one example of a vaporizer configuration 1100 consistent with the present disclosure. The illustrated example embodiment includes a vaporizer 1010a, a level sensor 1102 and a t-fitting 1104. including a vaporizer 1010a and a level sensor consistent with the present disclosure. In general, hydrogen peroxide solution, e.g., from the secondary supply 1006 (FIG. 9) is provided to the vaporizer 1010a through a conduit coupled to the vaporizer 1010a by a fitting. The hydrogen peroxide solution enters an interior chamber 1110 of the vaporizer 1010a, where it is vaporized by heat generated by one or more heating elements 1112 to provide HPV. The HPV enters the t-fitting 1104 and is moved by pressurized air from the blower, e.g., blower 1032, to the decontamination chamber 108b.

In the illustrated example embodiment, the vaporizer 1010a is constructed from a block 1114 of thermally conductive material, e.g., aluminum. The chamber 1110 is defined by the surfaces of a central bore 1116 extending through the block 1114. A first 1118 end of the bore 1116 is sized and configured, e.g., with threads, to receive the fitting 1108 and the second end 1120 of the bore 1116 is sized and configured, e.g., with threads, to receive the t-fitting 1104.

The heating elements 1112 are disposed in associated bores positioned radially outward from the chamber 1110 and extend beyond the length of the chamber 1110 at both ends thereof. The heating elements 1112 may take a variety of configurations. In some embodiments, the heating elements 1112 may be known heating cartridges and may be connected to an electrical power source through associated conductors (not shown). The heating elements 1112 may be configured to heat the block 1114 to a temperature of between about 100° C. and 150° C. to vaporize hydrogen peroxide entering the chamber 1110. In some embodiments, the heating elements 1112 may be configured to heat the block 1114 to a temperature of about 143° C.

The level sensor 1102 is coupled to the vaporizer 1010a and has a probe end 1122 that intersects the chamber 1110. If fluid builds up in the chamber 1110, e.g., due to condensation of HPV or failure of the vaporizer 1010a to vaporize the hydrogen peroxide solution, the level sensor 1102 provides an output to the controller 1034. In response to the output, the controller 1034 may disable the pump 1004 and/or the pump 1008 to prevent additional hydrogen peroxide solution from be provided to the vaporizer 1010a.

In the illustrated example embodiment, block 1114 includes a level sensor bore 1202 extending transversely to the chamber 1110 and intersecting the chamber 1110. The level sensor bore 1202 is sized and configured, e.g., with threads, to receive the probe end 1122 of the level sensor 1102. At the probe end 1122 of the level sensor 1102, first 1302, and second 1304 conductive probes are held in a spaced apart relationship and in fluid communication with the chamber 1110. A signal representative of the resistance between the first 1302 and second 1304 probes may be provided as the output of the level sensor 1102. In the absence of any fluid in the chamber 1110, a measurement of the resistance between the first 1302 and second 1304 probe provides a first output, e.g., an infinite resistance. If fluid builds up in the chamber 1110 and reaches the level of the probes 1302, 1304, the fluid creates a conductive path between the probes 1302, 1304 and the measured resistance between the probes 1302, 1304 drops significantly. The controller 1034 may disable the pump 1004 and/or the pump 1008 to prevent additional hydrogen peroxide solution from being provided to the vaporizer 1010a when the resistance between the first 1302 and second 1304 probes drops below a predetermined threshold.

Figure 14:
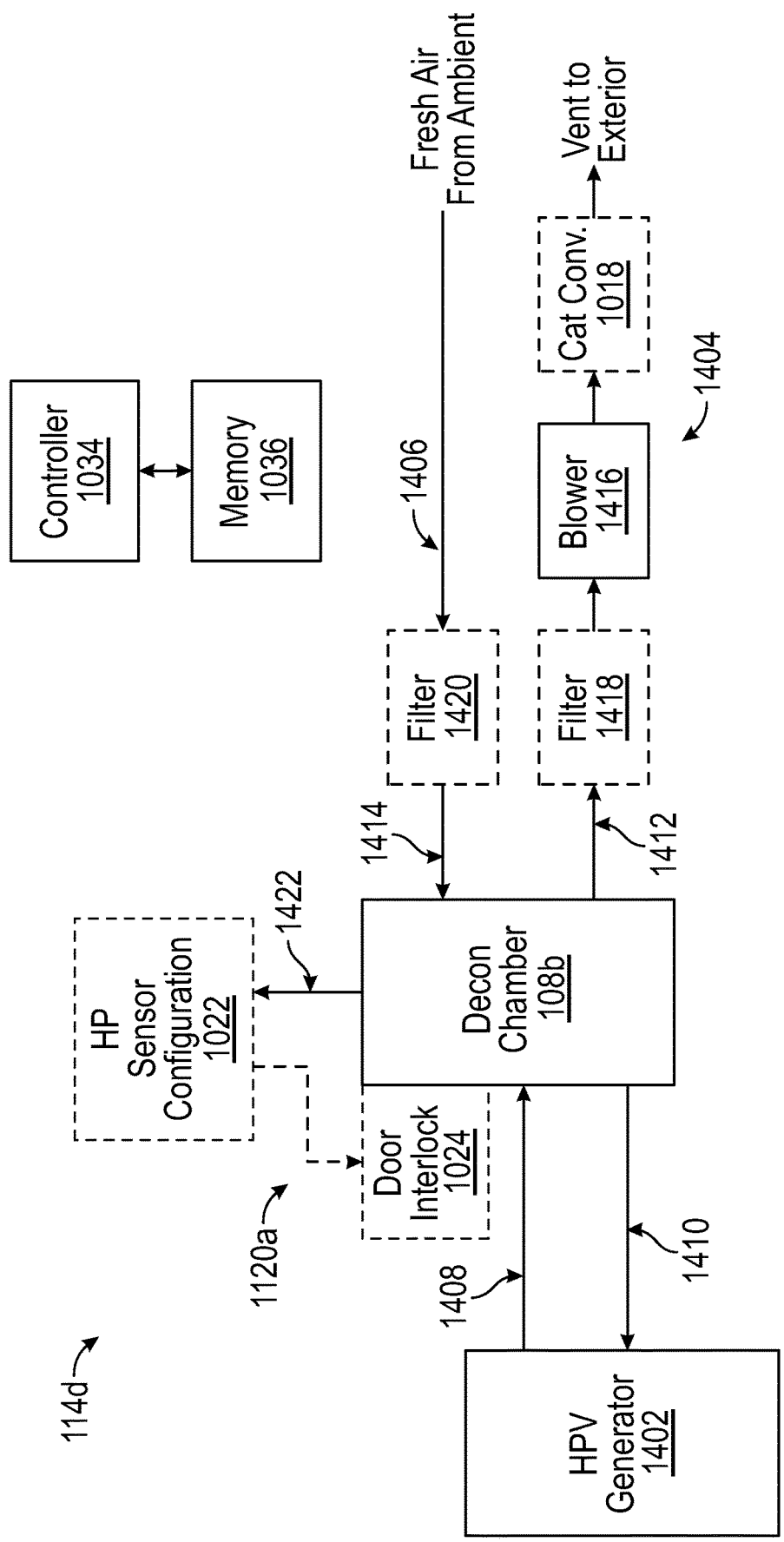
FIG. 14 is a block diagram of another example embodiment of a system consistent with the present disclosure.

Turning now to FIG. 14, there is illustrated another example embodiment of a decontaminant generator system 114d consistent with the present disclosure coupled to a decontamination chamber 108b. In the illustrated example embodiment, the decontaminant generator system 114d includes: an HPV generator 1402, a venting configuration 1404, a venting air intake configuration 1406; an optional door interlock configuration 1020a. The system may include a controller 1034 coupled to the components of the system for controlling operation of the components, e.g., in response to outputs from various sensors (not shown) and/or in response to computer readable instructions stored in a non-transient memory 1036. For clarity and ease of illustration, the connections between the controller 1034 and the system components and sensors are not shown. Also, although the example embodiment 114d shown in FIG. 14 will be described herein in connection with the decontamination chamber 108b, the illustrated configuration may be used in with any enclosure 102 and decontamination chamber 108 consistent with the present disclosure.

In general, the decontaminant generator system 114d includes separate paths for providing HPV to the decontamination chamber 108b during a decontamination cycle, and for degassing the decontamination chamber after a decontamination cycle. In a decontamination cycle HPV is generated by the HPV generator 1402, e.g., as described above in connection with FIG. 10 or using a commercially available system such as the Bioquell L-4 VPHP generator commercially available from Bioquell, Inc. of Horsham, Pennsylvania, USA. HPV is provided from the HPV generator 1402 to the decontamination chamber 108*b* on a first HPV path 1408 and then recycled HPV is drawn from the decontamination chamber 108*b* and returned to the HPV generator 1402 through a second HPV path 1410. The recycled HPV is combined in the HPV generator 1402 with the HPV on the first HPV path 1408 in a closed loop configuration. During a decontamination cycle, air flow from the decontamination chamber 108*b* to/from a venting path 1412 of the venting configuration 1404 and an air intake path 1414 of the air intake configuration 1406 is blocked, e.g., by closing associated valves (not shown) in response to control signals from the controller 1034.

During degassing of the decontamination chamber 108*b*, the HPV generator 1402 is disabled and air flow to/from the first 1408 and second 1410 HPV paths is blocked. Air flow is then enabled from the decontamination chamber 108*b* to/from a venting path 1412 of the venting configuration 1404 and an air intake path 1414 of the air intake configuration 1406. The venting configuration 1404 draws HPV from the decontamination chamber 108*b* and vents it to the exterior. In the illustrated example embodiment, the venting configuration 1404 includes a blower 1416 for drawing HPV from the decontamination chamber 108*b*, an optional filter 1418 and an optional catalytic converter 1018. The blower 1416 may be any known blower. The filter 1418 may be a HEPA filter for filtering contaminants from the HPV drawn from the decontamination chamber 1418. The catalytic converter 1018 may be configured as described above in connection with FIG. 10.

The air intake configuration 1406 provides a path for fresh air flow into the decontamination chamber 108*b* during degassing. In the illustrated embodiment, the air intake configuration 1406 includes an optional filter 1420. The filter 1420 may, for example, be a HEPA filter for filtering contaminants from the ambient air before the air enters the decontamination chamber 108*b*. During degassing negative pressure in the decontamination chamber 108*b* established by the blower 1416 draws air into the decontamination chamber 108*b* through the air intake configuration 1420. The blower 1416 then draws HPV from the decontamination chamber 108*b* and out to the exterior.

During decontamination and degassing, the door interlock configuration 1120*a* maintains the door, e.g., door 112*b* (FIG. 9), to the decontamination chamber 108*b* in a locked state until the hydrogen peroxide in the decontamination chamber 108*b* drops to a safe level. In general, the door interlock configuration 1120*a* may operate as described above in connection with the door interlock configuration 1120 shown in FIG. 10. In the illustrated example embodiment, the HP sensor configuration 1022 receives a sample of the air within the decontamination chamber 108*b* through a sampling path 1422 and couples the air to one or more hydrogen peroxide sensors. The door interlock 1024 is responsive to the hydrogen peroxide sensors in the HP sensor configuration 1022 to control the lock state of the door to the decontamination chamber 108*b*.

Figure 15:
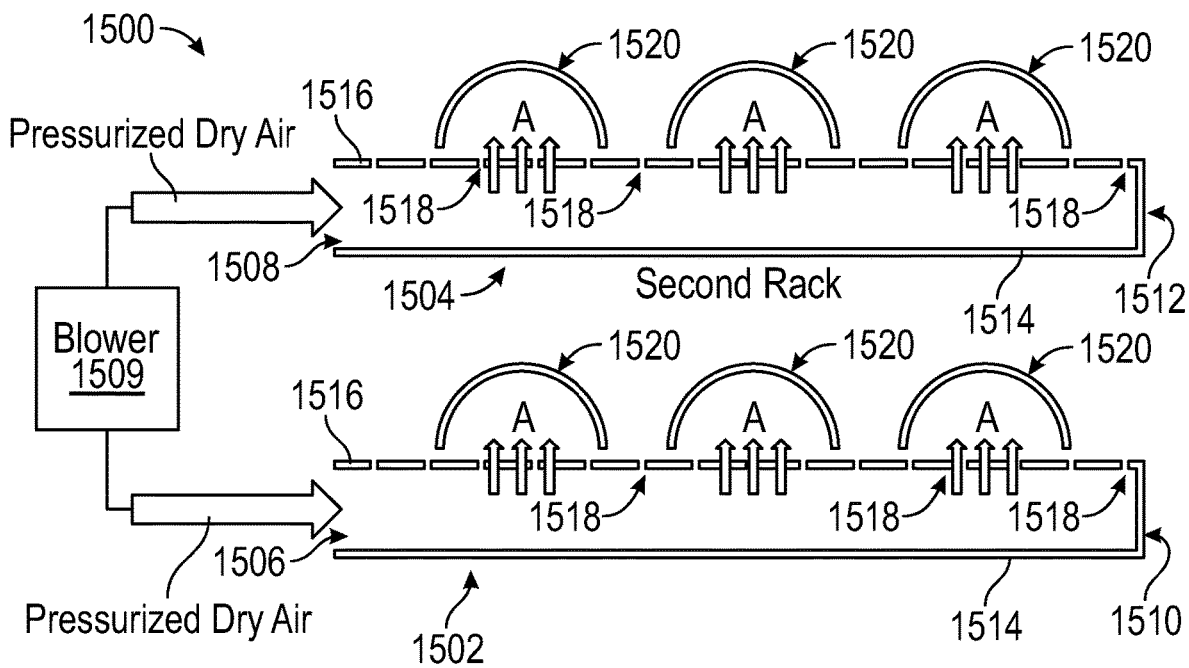
FIG. 15 diagrammatically illustrates one example embodiment of a rack configuration for drying patient care equipment consistent with the present disclosure.

FIG. 15 illustrates one example embodiment of a rack configuration 1500 for drying patient care equipment consistent with the present disclosure. The illustrated rack configuration 1500 includes a first rack 1502 and a second rack 1504. The first rack 1502 is positioned beneath the second rack 1504. The first 1502 and second 1504 racks may be provided in place of, or in addition to, shelves 316, 316*b* of a fixed or portable shelving structure useful in any embodiment 100, 100*a*, 100*b* of a decontamination system described herein.

In the illustrated example, the first 1502 and second 1504 racks are configured as elongate perforated ducts. The ducts may have any cross-sectional shape and have an open end 1506, 1508 for receiving pressurized dry air from a blower 1509, e.g., provided in the decontaminant generator system 114, 114*a*, 114*b*, and a closed end 1510, 1512. The open ends 1506, 1508 of the duct may be separately fluidly coupled to an output of the blower 1509 for receiving the pressurized dry air and/or they may be coupled together so that one coupling to the blower 1509 may provide pressurized dry air to the open end 1506, 1508 of both ducts. Each of the ducts also has a top surface 1514 and a bottom surface 1516. The patient care equipment may be supported on or adjacent the top surface 1516 each duct and the top surface 1516 of each duct and may include a plurality of openings 1518. The bottom surface 1514 of each duct may be continuous and devoid of any openings.

In the example shown in FIG. 15, patient care equipment is diagrammatically illustrated as masks 1520, e.g., N95 masks, supported on or adjacent the top surfaces 1516 of the ducts. As shown, the pressurized dry air may enter the open ends 1506, 1508 of the ducts and then pass upwardly through the openings 1518 in the top surfaces 1516 of the ducts toward the interior of the masks 1520, e.g., as indicated by arrows A, and also around the exterior of the masks 1520. This configuration has been found to provide an approximately 50% reduction in drying time compared to allowing dry air to passively or actively flow around the exterior patient care equipment.

Figure 16:
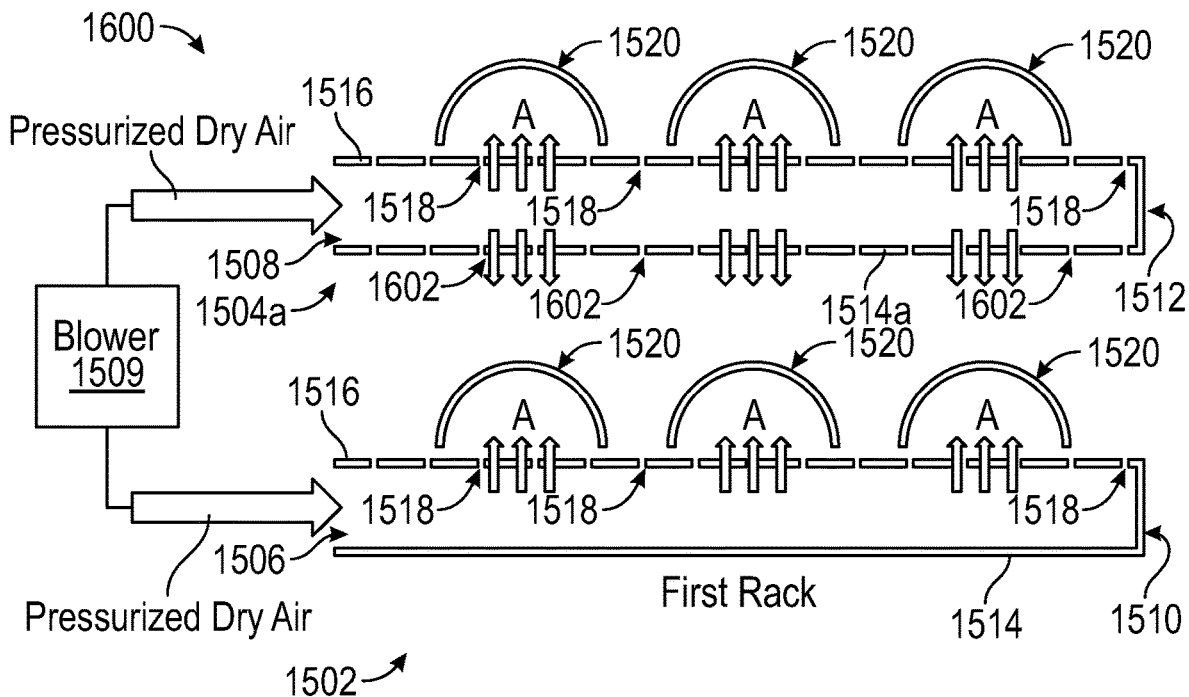
FIG. 16 diagrammatically illustrates another example embodiment of a rack configuration for drying patient care equipment consistent with the present disclosure.

In some embodiments, instead of a continuous bottom surface 1514 devoid of openings, one or more of the racks may having openings in its bottom surface 1514 to direct pressurized dry air toward patient care equipment supported beneath the rack. FIG. 16, for example, illustrates an example embodiment 1600 supporting patient care equipment illustrated as masks 1520 and including first 1502 and second 1504*a* racks similar to the racks shown in FIG. 15, except that the second rack 1504*a* includes openings 1602 in a bottom surface 1514*a* thereof. In addition to the pressurized dry air passing upwardly through the openings 1518 in the top surfaces 1516 of the ducts toward the interior of the masks 1520, pressurized air passes downwardly through the openings 1602 in the bottom surface 1514*a* of second rack 1504a toward the exterior surfaces of the masks 1520 supported on the first rack 1502. This further reduces the drying time for the patient care equipment on the first rack.

Figure 17:
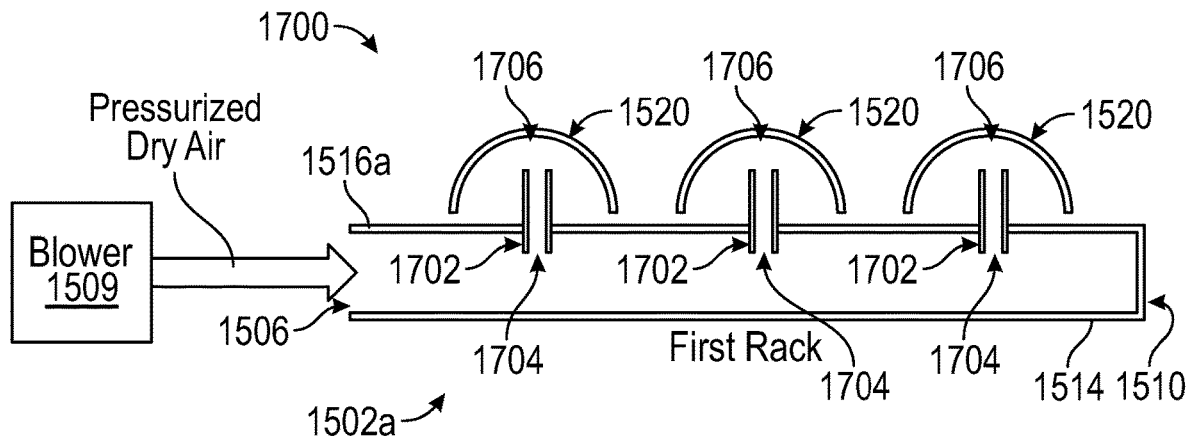
FIG. 17 diagrammatically illustrates another example embodiment of a rack configuration for drying patient care equipment consistent with the present disclosure.

In some embodiments, instead of openings in a top surface 1516 that direct pressurized air toward an interior of patient care equipment such as masks 1520, one or more of the racks 1502, 1504, 1504*a* may include a connecting duct defining one or more discrete openings for directing air toward the interior of the masks 1520. FIG. 17, for example, illustrates an example embodiment 1700 supporting patient care equipment illustrated as masks 1520 and including a rack 1502*a* similar to the rack 1502 shown in FIG. 15, except that the openings in the top surface of the rack 1502 are replaced by a connecting duct 1702 for directing the pressurized air toward the interior of the masks 1520. In the illustrated example embodiment, each of the connecting ducts 1702 is shown as a pipe having a first end 1704 disposed in the duct, i.e., between the top 1516*a* and bottom 1514 surface of the duct, and a second end 1706 positioned above the top surface 1516*a* of the duct in the interior of the mask 1520. This configuration directs a greater amount of the pressurized air toward the interior of the masks.

Although the connecting ducts 1702 in the illustrated example are simple pipes, a connecting duct 1702 may take a variety of configurations consistent with the present disclosure. In some embodiments, for example, the portion of the connecting duct 1702 above the top surface 1516*a* of the duct may include a plurality of openings therein for directing the pressurized air in different associated directions toward the interior of the masks 1520. In addition, or alternatively, the portion of the connecting duct 1702 above the top surface 1516*a* of the duct may be shaped, e.g., in a semi-circular configuration, to support and/or retain the masks 1520. Also, the top surface 1516*a* of the duct may not include any other openings therein, as shown, or openings may also be provided in the top surface to direct pressurized air around the exterior surfaces of the masks 1520.

Often rooms have shared work surfaces and require touching shared devices. Viruses survive on porous and non-porous surfaces for days to weeks; coronaviruses survive on surfaces at ambient temperature (~20° C.) for up to several weeks depending on humidity. Additional evidence suggests the SARS-CoV-2 virus survives on surfaces for up to 1 week at ambient temperature. Median time from exposure to infection in an individual for COVID-19 is approximately 5 days, and the disease is spread, at least in part, by pre-symptomatic but contagious individuals. Individuals infected with respiratory infections, like COVID-19, spread infectious material that settles on interior surfaces. Once there, infectious particles remain and can infect other individuals in the same area. Therefore, civilian and government leadership may not have appropriate time to react to staff testing positive in time to control the disease spread through team members.

There is thus a need to decontaminate interior spaces, which can contain porous materials, including paper, wood, and soft surfaces (e.g., carpet, cubicle walls). Common decontamination solutions are excellent surface decontaminants (e.g., non-porous surfaces); however, they may be unable to effectively decontaminate, without saturating or destroying, many porous materials. Removing materials, like paper or other porous materials, from a contaminated area can expose individuals to infectious agents.

To address these concerns, in some embodiments, a system and method consistent with the present disclosure may be configured as a portable, self-contained mobile interior decontamination system (MIDS) to decontaminate an interior facility, a small office or room. The system may use hot-air decontamination (HAD) to flood a single interior space (e.g., 200 ft$^2$ room of ~2000 ft$^3$) with appropriate environmental conditions to accelerate viral decontamination, without harm to sensitive or electronics equipment. By flooding heat throughout the interior space and/or portions of the space, virucide conditions are reached throughout the space, allowing for decontamination of materials, including porous materials like papers, wood etc., and soft surfaces such as carpet and cubicle walls, with minimal individual exposure. In some embodiments, no other decontaminant other than hot air may be required to decontaminate surfaces within the room to a desired decontamination level.

For example, thermal inactivation of coronaviruses accelerates as temperatures increase. Coronaviruses survive for days to weeks on surfaces at refrigeration (4° C., ~40° F.) or ambient (20° C., 69° F.) temperatures. As temperatures increase, viral inactivation accelerates. At 40° C. (104° F.), viral inactivation occurs in hours. In laboratory studies, coronaviruses lose 3-logs of infectivity at 20° C. (69° F.) over 4-28 days; however, at 40° C. (104° F.) coronaviruses lose 3-logs of infectivity over 6-48 hours (varies based on humidity). At 70° C. (158° F.), coronaviruses lose 3-logs of infectivity in less than 60 minutes.

In some embodiments, a MIDS consistent with the present disclosure targets air temperatures between 40-48° C. (104-120° F.) to align with UL product standards for commercial and household electronics. Products (e.g., thin line keypads, panels) are functionally tested up to 120° F. (49° C.). These temperatures will accelerate viral inactivation, allowing spaces to return to operational readiness in a matter of hours.

Figure 18:
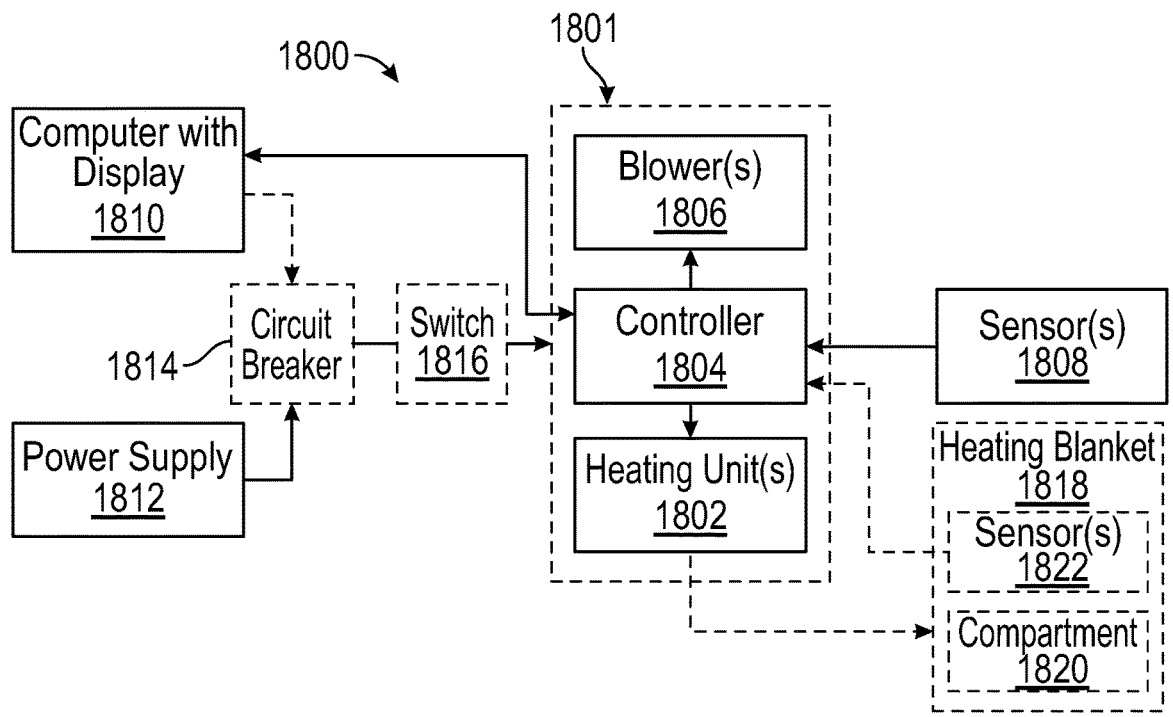
FIG. 18 is a block diagram of one example embodiment of a system consistent with the present disclosure.

FIG. 18 is a block diagram of one example embodiment of a MIDS system 1800 consistent with the present disclosure. The illustrated embodiment 1800 includes a hot air generator portion 1801 including one or more heating unit(s) 1802, a controller 1804 and one or more blowers 1806. The system may also include sensors 1808 configured to be coupled to the controller 1804, a computer with a display device 1810 and a plurality of cables for connecting one or more circuits of an electrical power supply 1812 to the system. In some embodiments, the system 1800 may require significant current and supply of the required current may require supply from more than one independent electrical circuits, e.g., if the power supply 1812 is a conventional line current supply providing circuits at 120/220 VAC. Each electrical circuit may be coupled to the system through an associated circuit breaker 1814 or switched power distribution unit (PDU) and/or a manual on/off switch 1816.

In the illustrated embodiment, the optional circuit breaker 1814 is coupled to, and controllable by, the computer with display 1810 to allow a user to remotely disable power to the hot air generator portion 1801. In addition, or alternatively, a user may be able to manually disconnect power to the hot air generator portion 1801 using the manual switch 1816 provided in one of the cables coupling the power supply 1812 to the hot air generator portion 1801. The computer with display 1810 and/or the switch 1816 may be positioned remotely, e.g., in a different room, from the hot air generator portion 1801 so that power to the hot air generator portion 1801 may be controlled remotely.

The system 1800 may use commercially available off-the-shelf technology. In some embodiments, heating unit(s) 1802 may be conductive, infrared and/or other heating units. In some embodiments, the heating units 1802 may be configured as a scalable construction or pest-control grade-heaters, residential- or commercial-grade heaters, and/or combination heat/humidity devices (e.g., wallpaper removers). The blowers 1806 may be known blowers including fans for distributing hot air heated by the heating units 1804 throughout a space to be decontaminated. Integrated and/or additional fans may be incorporated to circulate heat throughout the space efficiently and ensure HAD conditions are maintained throughout test locations.

The sensors 1808, e.g., one or more known thermo-hygrometers, may be configured for monitoring conditions throughout the room (or decontamination chamber, e.g., 108, 108*a*, 108*b*) to ensure full coverage of a target area at a desired temperature and, in some embodiments, a target humidity. One or more of the sensors 1808 may be integrated sensors coupled to a controller 1804 of the MIDS, e.g., using a wired connection. The controller 1804 controls the heating unit(s) 1802 and the blower(s) 1806 to establish a desired target temperature in the space to be decontaminated in response to the outputs of the sensors indicating the temperature in the vicinity of the sensors.

In the illustrated embodiment all of the sensors 1808 are wired to the controller 1804. One or more of the sensors 1808 may include a visual indicator to visually identify when a desired level of decontamination has been achieved by the MIDS system 1800. In some embodiments, the sensor outputs may be provided from the controller 1804 to the computer and display 1810 for displaying a heat map of the space indicating the temperature reported by each sensor in the space, thereby providing the user with a visual indication of the temperature. The computer with display 1810 may also be coupled to the controller 1804 for managing the controller 1804, e.g., for initiating a decontamination cycle, setting a target temperature and/or a target time for a decontamination cycle, etc.

In some embodiments, the system may include a heating blanket 1818 or covering configured to wrap around a compartment 1820 containing sensitive documents or other materials. The blanket may enclose compartment in a space and be configured to use conductive, infrared and/or hot air to heat the compartment 1820. In the illustrated example, embodiment, the blanket is coupled to the heating unit 1802, e.g., by a hose that provides hot air to a space inside the blanket containing the compartment 1820. In other embodiments, the heating blanket 1818 may be coupled to directly to the controller 1804 and the controller 1804 may provide power to conductive or infrared heating elements in the blanket 1818 to generate heat. Sensors 1822 provided in the space defined by the heating blanket 1818 and containing the compartment 1820 may be coupled to the controller 1804 for providing outputs indicating the temperature in the space around the compartment 1820. The controller 1804 may control the heating blanket 1818 or the heating unit(s) 1802 to establish a desired target temperature around the compartment 1820. In some embodiments using a heating blanket 1818, the additional sensors 1808 and/or the blowers 1806 may not be needed, e.g., if decontamination is provided only to the compartment within the heating blanket.

Externally heating a compartment or decontamination chamber also provides advantages when combined with providing an internal decontaminant such as HPV in the interior of the compartment or chamber. For example, in an embodiment providing an internal decontaminant in a decontamination chamber as described in connection with FIGS. 1-12, external heating may be applied to the decontamination chamber 108, 108a, 108b to increase the internal temperature of the decontamination chamber 108, 108a, 108b. In some embodiments, for example, one or more optional heating elements 120 (See FIG. 1), such as a heat tape or heat cable, may be applied to the exterior of the decontamination chamber 108, 108a, 108b to increase the internal temperature of the decontamination chamber 108, 108a, 108b to about 50 C. The heading elements may be applied to all sides of the decontamination chamber 108, 108a, 108b or to fewer than all sides of the decontamination chamber 108, 108a, 108b. Heating the decontamination chamber 108, 108a, 108b externally allows effective decontamination without subjecting an internal decontaminant vapor or spray, e.g., HPV, to high temperatures that would destroy the vapor or spray. Also, heating the decontaminant chamber 108, 108a, 108b externally, as opposed to internally, is efficient from a power and vapor consumption standpoint.

Figure 19:
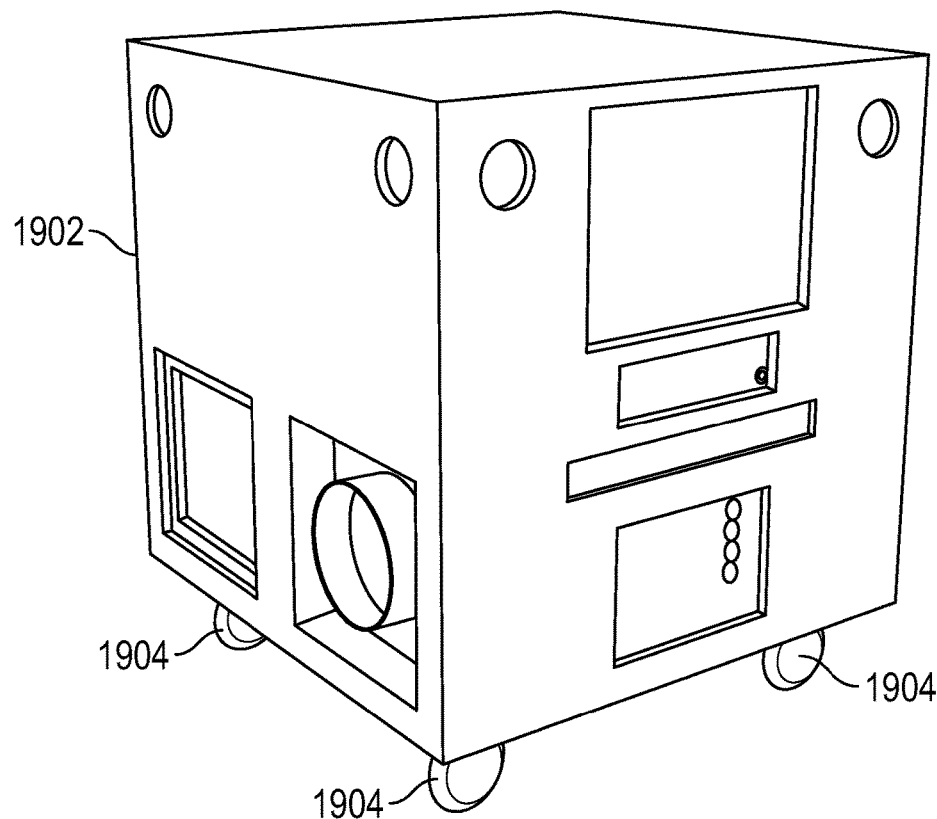
FIG. 19 is a perspective view of one example of a container for a system consistent with the present disclosure.

A MIDS system consistent with the present disclosure may be portable. In some embodiments, the components of the system may be configured for packing in one or more cases, e.g., pelican cases. As shown in FIG. 19, in some embodiments, the hot air generator portion 1801 may be packaged in a container 1902 supported by wheels 1904 for convenient moving into a space to be decontaminated. The container 1902 may also include compartments for storing the sensors 1804, the computer with display 1810, the circuit breaker 1814, the switch 1816, sensors 1808, heating blanket 1818, sensors 1822, and/or required cables for connecting components and power.

In some embodiments used for decontamination of large spaces, a plurality of the systems 1800 may be operated in parallel or multiplexed for decontaminating the entire space. For example, a plurality of systems 1800 may be independently operated in a space, or one system 1800 may be configured for controlling other systems 1800 as nodes to establish a desired target temperature throughout the space. In some embodiments, for example, a controller 1804 of one system may be programmed to receive information from sensors 1808 of other systems 1800 and control the other systems 1800 to establish the desired target temperature.

Figure 20:
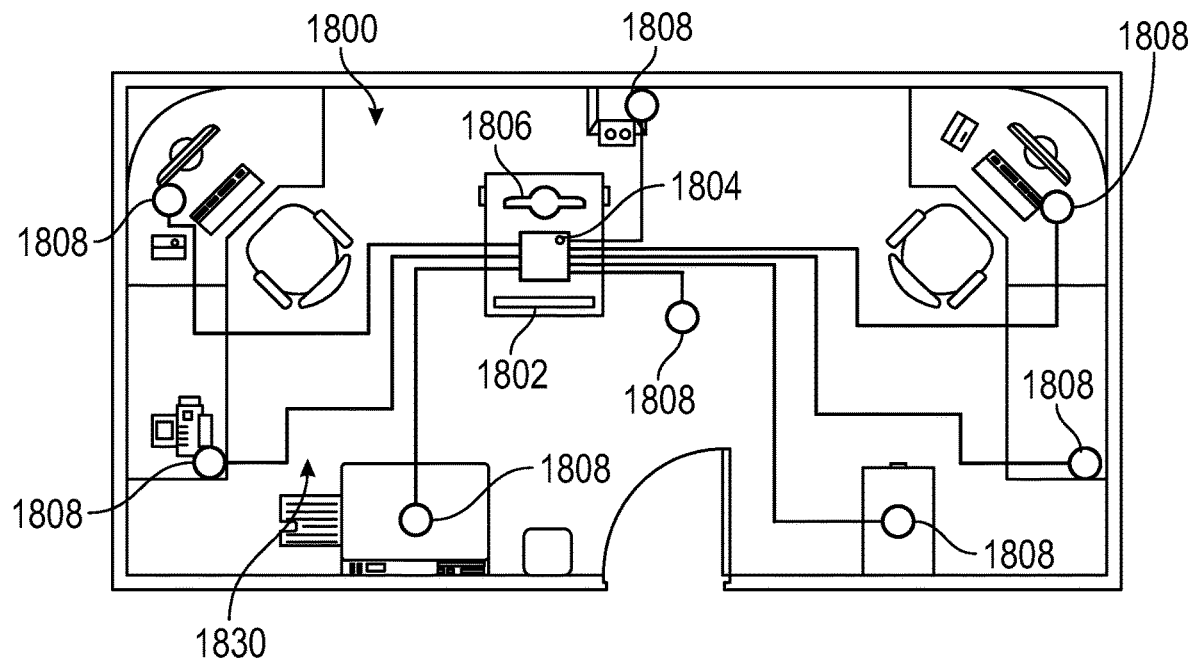
FIG. 20 diagrammatically illustrates one example of embodiment of a system consistent with the present disclosure in target area configured as an office space.

FIG. 20 diagrammatically illustrates one example of a MIDS system 1800 in target area 1830 configured as an office space. The MIDS system 1800 allows an individual to enter a potentially contaminated interior space or target area 1830 wearing limited personal protective equipment (PPE), set up the MIDS system, and initiate a decontamination cycle. The MIDS system ensures minimal interaction with contaminated space and items within the space, reducing risk to the decontamination team.

In some embodiments, a MIDS system 1800 consistent with the present disclosure provides two variables that can be used to control the depth of decontamination: time and temperature. The MIDS system 1800 allows the user to choose operation times, with longer times correlated to reduced risk, but possibly at a loss of operational readiness. Even at relatively short times (6-8 hours) at elevated temperatures, coronavirus infectivity is decreased by 1-4 logs The MIDS system 1800 allows for additional flexibility, allowing variability of the temperature used in decontamination. Moderate temperature inactivation (40-48° C., 104-119° F.) can be applied in locations that require lower temperatures. If the facility can withstand higher temperatures (>55° C., >125° F.), then the decontamination process can be completed faster with the same log kill. Multiple MIDS systems can also be run in parallel, allowing higher temperatures and faster temperature ramp rates in larger interior spaces.

Figure 21:
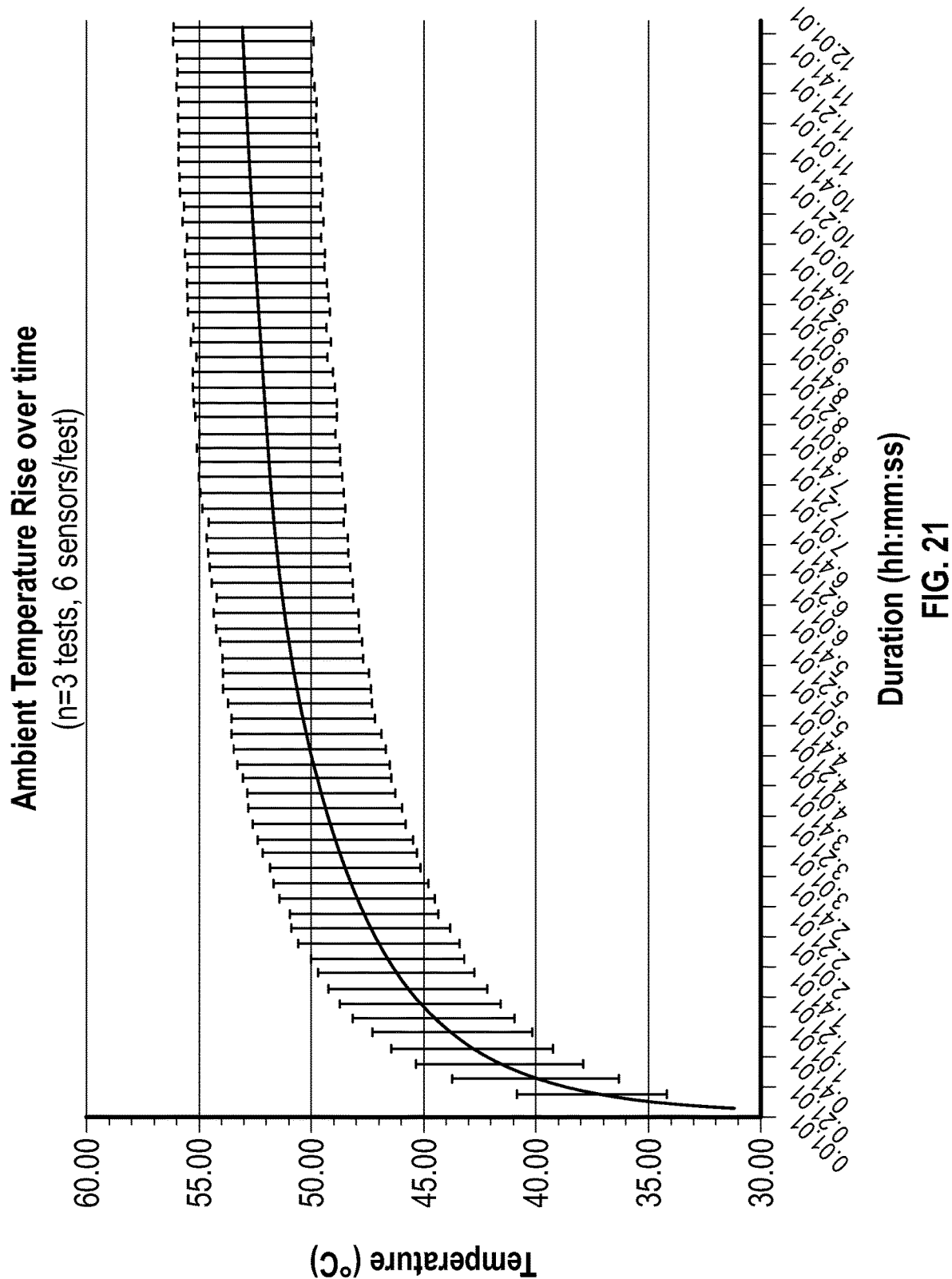
FIG. 21 is a plot of temperature vs. time illustrating operation of an example embodiment consistent with the present disclosure.

In some embodiments, the MIDS system 1800 may be configured to ramp temperatures by 20° C. to 40° C. over ~3-3.5 hours. Temperature may be maintained between 40° C.-55° C. for as long as necessary by interior thermocouples. The innovative use of modular, quick-connect sensors 1308 that can be placed in difficult to reach areas, assures full coverage of the entire targeted space. In one example embodiment used in an approximately 1000 ft$^3$ room, a single MIDS system 1800 consistent with the present disclosure using a hard-wired sensor suite of 6 thermo-hygrometers was used to generate HAD in the room. FIG. 21 is a plot of temperature vs. time illustrating the ambient temperature rise in the room vs. time in three independent tests.

While the foregoing description includes various operations for decontaminating patient care equipment, such as N95 respirators and face shields, and interior spaces according to example embodiments consistent with the present disclosure, it is to be understood that not all of the operations depicted are necessary for other embodiments. Indeed, it is fully contemplated herein that in other embodiments of the present disclosure, the example operations described above for decontaminating N95 respirators and face shields, and/or other operations described herein, may be combined in a system and method consistent with the present disclosure. Thus, claims directed to features and/or operations that are not exactly shown in one drawing or described in one example are deemed within the scope and content of the present disclosure.

There is thus provided systems and methods for decontamination of patient care equipment in a decontamination chamber. There is also provided mobile interior decontamination system (MIDS) and methods. MIDS floods an interior space (e.g., room of ~2000 ft$^3$) with hot air, which significantly accelerates viral decontamination. By flooding heat into the space, sterilizing conditions are achieved, decontaminating porous materials, including papers, office equipment and even money. Unlike wet decontaminants, this process is also safe for sensitive electronic equipment and does not require hazardous chemicals or cleaning agents. In addition to being mobile, in some embodiments MIDS uses standard electrical power (110/220, 50/60 Hz), and operates autonomously.

According to one aspect of the disclosure there is thus provided a system for decontamination of patient care equipment, the system a portable enclosure; a decontaminant distributor disposed in the enclosure for distributing a decontaminant in the enclosure; and a decontaminant generator system. The decontaminant generator system includes a decontaminant generator for providing the decontaminant to the decontaminant distributor. The decontaminant generator is removably coupled to the decontaminant distributor at an exterior of the enclosure for allowing the decontaminant generator to be removed and connected to another decontaminant distributor associated with another system for decontamination of patient care equipment.

According to another aspect of the disclosure, there is provided a system for decontamination of patient care equipment, the system including: a portable enclosure; a partition in the enclosure to define a decontamination chamber and an anteroom; a decontaminant distributor disposed in the decontamination chamber for distributing a decontaminant in the decontamination chamber; a decontaminant generator system, the decontaminant generator system comprising a decontaminant generator configured to generate a vaporized decontaminant, the decontaminant generator being removably coupled to the decontaminant distributor at an exterior of the enclosure for allowing the decontaminant generator to be removed and connected to another decontaminant distributor associated with another system for decontamination of patient care equipment; and an air agitation system for agitating the decontaminant in the enclosure.

According to another aspect of the disclosure, there is provided a system for decontamination of patient care equipment, the system including: a portable enclosure; a decontaminant distributor disposed in the enclosure for distributing a decontaminant in the enclosure; a decontaminant generator system coupled to the decontaminant distributor, the decontaminant generator system comprising a decontaminant generator configured to generate a vaporized decontaminant; and an air agitation system for agitating the decontaminant in the enclosure.

According to yet another aspect of the disclosure, there is provided a method of decontaminating patient care equipment including: placing the patient care equipment in a portable enclosure having a decontaminant distributor disposed therein; operating a decontaminant generator coupled to the decontaminant distributor to generate and distribute a decontaminant in the enclosure; the decontaminant generator being removably coupled to the decontaminant distributor at an exterior of the enclosure; disconnecting the decontaminant generator from the decontaminant distributor; and connecting the decontaminant generator to another system for decontamination of patient care equipment.

According to another aspect of the disclosure, there is provided a method of decontaminating patient care equipment including: placing the patient care equipment in a portable enclosure having a decontaminant distributor disposed therein; placing at least one chemical indicator card in the enclosure; operating a decontaminant generator coupled to the decontaminant distributor to generate and distribute a decontaminant in the enclosure; the decontaminant generator being removably coupled to the decontaminant distributor at an exterior of the enclosure; visually observing the at least one chemical indicator card to confirm a desired level of decontamination has been provided to the patient care equipment; disconnecting the decontaminant generator from the decontaminant distributor; and connecting the decontaminant generator to another system for decontamination of patient care equipment.

According to another aspect of the disclosure, there is provided a method of decontaminating the surfaces in a room including: moving a decontaminant generator into the room, the decontaminant generator being portable and configured to generate heated air within the room at a temperature configured to decontaminate the surfaces in the room to a desired level of decontamination; operating the decontaminant generator to distribute the heated in the room; and visually observing at least one visual indicator to confirm a desired level of decontamination has been provided to the surfaces in the room.

According to still another aspect of the disclosure, there is provided a system for decontamination of surfaces of an enclosed space, the system including: a portable decontamination system including at least one heating unit; at least one blower for distributing air heated by the heater in the enclosed space, and a controller; and a plurality of sensors configured to be coupled to the controller be placed in the room at different locations remote from the heating unit. The controller is configured to receive outputs from the plurality of sensors and control the heater and the blower to establish a desired temperature in the vicinity of each of the sensors in the enclosed space in response to the outputs from the plurality of sensors.

According to yet another aspect of the disclosure, there is provided a method of decontamination of surfaces in an enclosed space, the method including: moving a decontaminant generator into the enclosed space, the decontaminant generator including at least one heating unit; at least one blower for distributing air heated by the heater in the enclosed space, and a controller; placing a plurality of sensors coupled to the controller at different locations in the enclosed space; and controlling the heater and the blower by the controller to establish a desired temperature in the vicinity of each of the sensors in response to the outputs from the plurality of sensors.

According to another aspect of the disclosure there is provided a system for decontamination of patient care equipment, the system including: a portable enclosure; a decontaminant distributor disposed in the enclosure for distributing a decontaminant in the enclosure; a decontaminant generator system coupled to the decontaminant distributor, the decontaminant generator system comprising a decontaminant generator configured to generate a vaporized decontaminant; a blower; and a rack configuration disposed in the enclosure for supporting patient care equipment. The rack configuration includes at least one rack comprising a duct having top and bottom surfaces and an open end for receiving pressurized air from the blower, at least one of the top and bottom surfaces having at least one opening therein for directing the pressurized air toward the patient care equipment.

According to another aspect of the disclosure there is provided a rack configuration for drying patient care equipment, the rack configuration including: at least one rack comprising a duct having top and bottom surfaces and an open end for receiving pressurized air, at least one of the top and bottom surfaces having at least one opening therein for directing the pressurized air toward the patient care equipment.

According to another aspect of the disclosure, there is provided a system for decontamination of patient care equipment, the system including: a portable enclosure; a decontaminant distributor disposed in the enclosure for distributing a vaporized decontaminant in the enclosure; a decontaminant generator system coupled to the decontaminant distributor, the decontaminant generator system comprising a decontaminant generator configured to generate the decontaminant; and an external heating element coupled to an exterior of the enclosure for heating the interior of the enclosure.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto.

Embodiments of the methods described herein may be implemented using a controller, processor and/or other programmable device. To that end, the methods described herein may be implemented on a tangible, non-transitory computer readable medium having instructions stored thereon that when executed by one or more processors perform the methods. Thus, for example, the memory 1036 may store instructions (in, for example, firmware or software) to perform the operations described herein. The storage medium, e.g. the memory 1036, may include any type of tangible medium, for example, any type of disk optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions.

It will be appreciated by those skilled in the art that any block diagrams herein represent conceptual views of illustrative circuitry embodying the principles of the disclosure. Similarly, it will be appreciated that any block diagrams, flow charts, flow diagrams, state transition diagrams, pseudocode, and the like represent various processes which may be substantially represented in computer readable medium and so executed by a computer or processor, whether or not such computer or processor is explicitly shown. Software modules, or simply modules which are implied to be software, may be represented herein as any combination of flowchart elements or other elements indicating performance of process steps and/or textual description. Such modules may be executed by hardware that is expressly or implicitly shown.

The functions of the various elements shown in the figures, including any functional blocks labeled as a controller or processor, may be provided through the use of dedicated hardware as well as hardware capable of executing software in association with appropriate software. The functions may be provided by a single dedicated processor, by a single shared processor, or by a plurality of individual processors, some of which may be shared. Moreover, explicit use of the term controller or processor should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

The term "coupled" as used herein refers to any connection, coupling, link or the like by which signals carried by one system element are imparted to the "coupled" element. Such "coupled" devices, or signals and devices, are not necessarily directly connected to one another and may be separated by intermediate components or devices that may manipulate or modify such signals.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" and/or "an" and/or "the" to modify a noun may be understood to be used for convenience and to include one, or more than one, of the modified noun, unless otherwise specifically stated. The terms "comprising", "including" and "having" are intended to be inclusive and mean that there may be additional elements other than the listed elements.

Although the methods and systems have been described relative to a specific embodiment thereof, they are not so limited. Obviously, many modifications and variations may become apparent in light of the above teachings. Many additional changes in the details, materials, and arrangement of parts, herein described and illustrated, may be made by those skilled in the art.

What is claimed is:

1. A system for decontamination of patient care equipment, the system comprising:
   a portable enclosure;
   a blower;
   a rack configuration disposed in the portable enclosure for supporting patient care equipment, the rack configuration including at least one rack comprising a duct having top and bottom surfaces and an open end for receiving pressurized air from the blower, at least one of the top and bottom surfaces having at least one opening therein for directing the pressurized air toward the patient care equipment;
   a partition in the portable enclosure to define a decontamination chamber and an anteroom, the anteroom including controls to start a decontamination cycle, and the partition being sealed to prevent a decontaminant from entering the anteroom from the decontamination chamber;

a sealable decontaminant chamber entry door in the partition for allowing access to the decontaminant chamber from the anteroom;

a sealable anteroom entry door for allowing access to the anteroom from an exterior of the portable enclosure, the sealable decontaminant chamber entry door and the sealable anteroom entry door being configured to seal the anteroom from the decontamination chamber and the exterior of the portable enclosure to establish the anteroom as a sealed airlock;

a decontaminant distributor comprising piping disposed in the interior of the decontamination chamber but not in the anteroom for distributing the decontaminant in the decontamination chamber and not in the anteroom; and a decontaminant generator system, the decontaminant generator system comprising a decontaminant generator for providing the decontaminant to the decontaminant distributor, the decontaminant generator removably coupled to the decontaminant distributor at an exterior of the portable enclosure for allowing the decontaminant generator to be removed and connected to another decontaminant distributor associated with another system for decontamination of patient care equipment.

2. A system according to claim 1, the system further comprising an air agitation system for agitating the decontaminant in the enclosure.

3. A system according to claim 1, wherein the decontaminant comprises vaporized hydrogen peroxide.

4. A system according to claim 1, the system further comprising a filter disposed in the sealable decontaminant chamber entry door and a cover for covering the filter during decontamination of patient care equipment.

5. A system according to claim 1 further comprising at least one chemical indicator card disposed in the portable enclosure to provide a visual indication of a level of decontamination provided to the patient care equipment.

6. A system according to claim 1, further comprising at least one heating element coupled to an exterior of the portable enclosure for heating an interior of a decontamination chamber portion of the enclosure.

7. A system according to claim 1 further comprising a door interlock configuration acting on the sealable anteroom entry door to maintain the sealable anteroom entry door in a locked state until the decontaminant in at least a portion of the decontamination chamber is below a predetermined level.

8. A system according to claim 1, wherein the decontaminant generator system is configured in a closed loop configuration for decontaminating the patient care equipment during a decontamination cycle and in an open loop configuration for degassing the enclosure after the decontamination cycle.

9. A system according to claim 1, wherein the decontaminant generator comprises a vaporizer having a chamber therein for vaporizing the decontaminant and wherein the system further comprises a level sensor for detecting fluid in the chamber.

10. A system according to claim 9, wherein the level sensor comprises first and second spaced probes in fluid communication with the chamber.

11. The system according to claim 9, wherein the decontaminant generator system further comprises:
a primary supply of the decontaminant and a secondary supply of the decontaminant, wherein:
the primary supply of the decontaminant is pumped into the secondary supply of the decontaminant;
the secondary supply of the decontaminant is pumped into the decontaminant generator; and
the decontaminant from the secondary supply is used for the decontamination cycle while the primary supply is replaced.

12. A system according to claim 1, wherein the at least one opening is in the top surface.

13. A system according to claim 12, wherein the at least one opening is defined by a connecting duct having a first open end above the top surface and a second open end in the duct between the top surface and the bottom surface.

14. A system according to claim 1, wherein the at least one opening is in the bottom surface.

15. A system according to claim 1, wherein the at least one rack comprises a first rack positioned beneath a second rack, and the at least one opening in the first rack is in the top surface of the first rack and the at least one opening in the second rack is in the top surface of the second rack.

16. A system according to claim 1, wherein the at least one rack comprises a first rack positioned beneath a second rack, and the at least one opening in the first rack is in the top surface of the first rack and the at least one opening in the second rack comprises at least one opening in the top surface of the second rack and at least one opening in the bottom surface of the second rack.

17. A method of decontaminating patient care equipment comprising:
placing the patient care equipment in the portable enclosure according to claim 1;
operating the decontaminant generator to generate and distribute the decontaminant in the portable enclosure;
disconnecting the decontaminant generator from the decontaminant distributor; and
connecting the decontaminant generator to another system for decontamination of patient care equipment.

18. A method according to claim 17, further comprising placing at least one chemical indicator card in the portable enclosure to provide a visual indication of a level of decontamination provided to the patient care equipment.

19. A method according to claim 17, the method further comprising agitating the air in the portable enclosure.

20. A method according to claim 17, further comprising energizing at least one heating element coupled to an exterior of the portable enclosure for heating an interior of a decontamination chamber portion of the enclosure.

21. A method according to claim 17, further comprising degassing the portable enclosure by operating a second blower.

* * * * *